US012691102B2

(12) United States Patent
Jung

(10) Patent No.: US 12,691,102 B2
(45) Date of Patent: Jul. 28, 2026

(54) COMPOSITION FOR PREVENTING OR TREATING CHRONIC KIDNEY DISEASE, COMPRISING COMPOUND THAT INDUCES EXPRESSION OF ANTI-AGING GENE KLOTHO

(71) Applicant: KLOTHO SCIENCES, Seongnam-si (KR)

(72) Inventor: Dong Ju Jung, Cheonan-si (KR)

(73) Assignee: KLOTHO SCIENCES, Seongnam-si (KR)

( * ) Notice: Subject to any disclaimer, the term of this patent is extended or adjusted under 35 U.S.C. 154(b) by 430 days.

(21) Appl. No.: 18/553,392

(22) PCT Filed: Apr. 1, 2022

(86) PCT No.: PCT/KR2022/004706
§ 371 (c)(1),
(2) Date: Sep. 29, 2023

(87) PCT Pub. No.: WO2022/211574
PCT Pub. Date: Oct. 6, 2022

(65) Prior Publication Data

US 2024/0216341 A1 Jul. 4, 2024

(30) Foreign Application Priority Data

Apr. 1, 2021 (KR) ........................ 10-2021-0042955
Mar. 31, 2022 (KR) ........................ 10-2022-0040453

(51) Int. Cl.
*A61K 31/423* (2006.01)
*A61K 9/00* (2006.01)
*A61P 13/12* (2006.01)

(52) U.S. Cl.
CPC .......... *A61K 31/423* (2013.01); *A61K 9/0056* (2013.01); *A61P 13/12* (2018.01)

(58) Field of Classification Search
CPC ...... A61K 31/423; A61K 9/0056; A61P 13/12
USPC .......................................................... 514/375
See application file for complete search history.

(56) References Cited

U.S. PATENT DOCUMENTS

2024/0358683 A1* 10/2024 Jung .................... A61K 31/423

FOREIGN PATENT DOCUMENTS

KR 20020089493 11/2002
KR 20170024522 3/2017
WO WO 2016/176473 11/2016

OTHER PUBLICATIONS

English abstract of KR 2017024522 A, translated on Dec. 17, 2025 (Year: 2025).*
Bradford et al., "High-throughput screens for agonists of bone morphogenetic protein (BMP) signaling identify potent benzoxazole compounds" *J. Biol. Chem.* 2019, 294(9), pp. 3125-3136.
International Search Report and Written Opinion issued in corresponding PCT Application No. PCT/KR2022/004706, dated Jul. 25, 2022 (English translation provided).
Kim et al., "Synthesis of benzoxazole derivatives as interleukin-6 antagonists" *Bioorganic & Medicinal Chemistry* 2017, 25(12), pp. 3127-3134.

* cited by examiner

*Primary Examiner* — Kristin A Vajda
(74) *Attorney, Agent, or Firm* — NORTON ROSE FULBRIGHT US LLP

(57) ABSTRACT

The present invention relates to a composition for the prevention or treatment of chronic kidney disease (CKD), comprising compounds that induce the expression of the anti-aging gene klotho. The compounds represented by Chemical Formula 1 according to the invention are highly effective in enhancing the expression of the Klotho gene, a gene associated with aging, and thus can be useful for a pharmaceutical composition or a food composition for the prevention, amelioration or treatment of CKD.

9 Claims, 18 Drawing Sheets

Specification includes a Sequence Listing.

COMPOSITION FOR PREVENTING OR TREATING CHRONIC KIDNEY DISEASE, COMPRISING COMPOUND THAT INDUCES EXPRESSION OF ANTI-AGING GENE KLOTHO

CROSS-REFERENCE TO RELATED APPLICATIONS

This application is a national phase application under 35 U.S.C. § 371 of International Application No. PCT/KR2022/004706, filed Apr. 1, 2022, which claims priority to Korean Patent Application No. 10-2021-0042955, filed Apr. 1, 2021, and Korean Patent Application No. 10-2022-0040453, filed Mar. 31, 2022, the entire contents of which applications are hereby incorporated by reference.

FIELD OF THE DISCLOSURE

The present invention relates to a composition for the prevention or treatment of chronic kidney disease (CKD) comprising a compound that induces the expression of the anti-aging gene klotho.

DESCRIPTION OF RELATED ART

Chronic kidney disease (CKD) is a disease state of kidney damage or decreased kidney function that lasts for more than three months and is recognized as a serious health problem worldwide. CKD is a growing healthcare issue in many countries due to its high prevalence and incidence, complications such as stroke, heart disease, diabetes, and infections, and rising healthcare costs due to an aging population and increasing prevalence of chronic diseases.

On the other hand, the fact that there may be genes capable of regulating aging in animals became known through senescence-accelerated mice (SAM) reported in 1981. These mice, which were accidentally made while crossing AKR/J series mice, aged much faster than mice of the same family, and these mice were confirmed to have mutations in several genes. Later, the discovery of a single group of aging-related genes was reported in the 1990s. The reported genes were genes that expressed an enzyme called DNA helicase in the RecQ family. It has been reported that, when mutations occur in these genes, the result that premature aging occurs or cancer is produced, which is known to be caused by affecting DNA repair. A single gene associated with aging is the klotho gene, which was reported in 1997. The klotho gene was accidentally discovered while creating an animal model for transgenic hypertension mice, but in mice that could not express this gene, premature aging occurred and their lives were shortened. More interestingly, the lifespan of mice that later increased the expression of this gene increased by 20.0 to 30.8% in males and 18.8 to 19.0% in females. This became the first opportunity to inform the world that the lifespan of mice can be increased or decreased depending on the expression of a single gene. In addition, the base sequence of the klotho gene was very similar among animals, and it was reported that it was about 98% identical between mice and humans. This indicates that lifespan can be regulated according to the expression of the klotho gene in humans as well.

In humans, the klotho gene is located on chromosome 13 and produces a membrane protein with a base sequence similar to β-glucosidase. The protein klotho is mainly expressed in renal tubular epithelial cells and brain choroid plexus, and has been reported to be expressed in some parathyroid glands. The klotho gene is a gene associated with various aging phenotypes, and in mice lacking the klotho gene, a syndrome similar to the aging process such as shortened lifespan, decreased activity, growth retardation, atherosclerosis, arterial calcification, osteoporosis, immature reproductive organs, infertility, skin atrophy, and emphysema occurs. In klotho mutant mice, atherosclerosis similar to Monckeberg type arteriosclerosis caused by aging in humans is observed in all arteries from the aorta to the arterioles, and angiogenesis and vasculogenesis are impaired.

The expression of klotho mRNA is significantly higher in kidney tissue than in other tissues, but the expression of klotho mRNA is decreased in the kidneys of mice in a disease model of hypertension, type 2 diabetes, diabetic nephropathy, and chronic renal failure. In mice with reduced klotho expression, the production of nitric oxide, which is a relaxation factor derived from vascular endothelium, decreases, and when the klotho gene is injected into Otsuka Long-Evans Tokushima fatty rat (OLETF) mice, which simultaneously have risk factors for many cardiovascular diseases, using a viral gene carrier, endovascular dysfunction is alleviated, the production of NO is increased, and blood pressure is lowered by suppressing vascular thickening and fibrosis. In addition, the klotho gene also affects glucose and insulin metabolism in mice, and statin, which is a representative therapeutic agent for hypercholesterolemia, increases the expression of klotho mRNA in renal proximal tubule cells. In mice with reduced klotho expression, osteopenia of low bone turnover states occurs due to impaired differentiation of both osteoblasts and osteoclasts, which is similar to the characteristics of bone loss and senile osteoporosis according to an increase in age in humans. Furthermore, in klotho mutant mice, abnormal elongation of the trabecular bone at the epiphysis area and abnormal trabecular bone tissue on micro-computerized tomography are observed, which is due to the disorder of the bone resorption process. Changes in clinical phenotypes caused by mutations in the klotho gene observed in humans are diverse. The functional variant of klotho (KL-VS) modification with mutations in three sites of the klotho gene exon2 is associated with lipid metabolism, blood pressure, lifespan, cognitive function, coronary artery disease and cerebrovascular disease, and microsatellite polymorphism and single base genetic polymorphism of the klotho gene are associated with bone density, and it has also been reported that the single base genetic polymorphism of the klotho gene in healthy adult women is associated with cardiovascular disease risk factors and bone density. Recently, the association between the klotho gene and Alzheimer's disease has also been reported in several papers. In Alzheimer dementia mouse models, it has been reported that overexpression of klotho increases the lifespan of mice by 30% and inhibits a reduction in cognitive function. Furthermore, it was observed that the production of amyloid beta protein in the brain was reduced by 50% by klotho expression. In humans, the expression level of klotho is inversely proportional to the progression of Alzheimer's disease, and a report was submitted that the klotho protein reduces the amount of inflammatory cytokines in the blood of patients with Alzheimer's disease.

Efforts have been continuously made to develop a material capable of inducing the expression of the klotho gene, which has such a clear senescence inhibitory effect. Among known materials, those reported to be able to induce the expression of klotho include rapamycin, vitamin D, statin, and the like. In 2012, a research team at Boston University reported three compounds that they found by screening for compounds capable of inducing the expression of the klotho gene using a library of 150,000 compounds in total.

SUMMARY OF THE INVENTION

The present inventors selected a compound called compound H, which has a structure that is highly likely to be developed as a pharmaceutical, among the compounds, confirmed through actual experiments that the compound can express the klotho gene in cells, and published the research results on its mechanism of action in a paper. Since then, the present inventors have conducted experiments to analyze the structure of compound H (Comparative Example 1), found the structural characteristics of the compound capable of inducing klotho expression, and based on this, made a new compound whose activity was increased by 10 times or more. In addition, the present inventors experimentally confirmed that the present novel compounds inducing the expression of the anti-aging gene klotho are useful for preventing or treating chronic kidney disease, thereby completed the present invention.

An object of the present invention is to provide a pharmaceutical composition for preventing or treating chronic kidney disease comprising a compound represented by Chemical Formula 1 or a pharmaceutically acceptable salt thereof.

Another object of the present invention is to provide a health functional food composition for preventing or improving chronic kidney disease, or a food composition comprising the compound represented by Chemical Formula 1 or a pharmaceutically acceptable salt thereof.

To achieve the objects, the present invention provides a pharmaceutical composition for preventing or treating chronic kidney disease comprising a compound represented by Chemical Formula 1 below or a pharmaceutically acceptable salt thereof as an active ingredient:

[Chemical Formula 1]

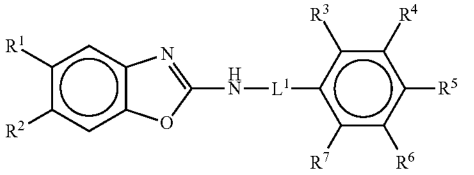

(in Chemical Formula 1, $L^1$ is a single bond or

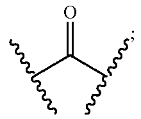

$R^1$ and $R^2$ are each —H, —OH, a $C_{1-10}$ straight or branched alkyl, or a $C_{6-8}$ arylamide, wherein the aryl of the arylamide may be substituted with one or more of a halogen, —$NO_2$ and a $C_{1-10}$ straight or branched alkyl halide;

$R^1$ and $R^2$ may form a $C_{6-8}$ aryl with a carbon atom to which they are linked; and $R^3$, $R^4$, $R^5$, $R^6$ and $R^7$ are each —H, a halogen, —$NO_2$ or a $C_{1-10}$ straight or branched alkyl).

In addition, the present invention provides a health functional food composition for preventing or improving chronic kidney disease comprising the compound represented by Chemical Formula 1 or a pharmaceutically acceptable salt thereof as an active ingredient.

Furthermore, the present invention provides a food composition for preventing or improving chronic kidney disease comprising the compound represented by Chemical Formula 1 or a pharmaceutically acceptable salt thereof as an active ingredient.

In addition, the present invention provides a method for preventing or treating chronic kidney disease comprising the step of administering or ingesting a composition containing the compound represented by Chemical Formula 1 or a pharmaceutically acceptable salt thereof as an active ingredient to a subject.

In addition, the present invention provides a use for preventing or treating chronic kidney disease of a composition comprising the compound represented by Chemical Formula 1 or a pharmaceutically acceptable salt thereof as an active ingredient.

The compound represented by Chemical Formula 1 according to the present invention has an excellent effect of improving the expression level of klotho gene, which is a gene related to aging, and can be usefully used as a pharmaceutical composition or food composition for preventing, improving or treating chronic kidney disease.

DETAILED DESCRIPTION OF THE INVENTION

Figure 1A:
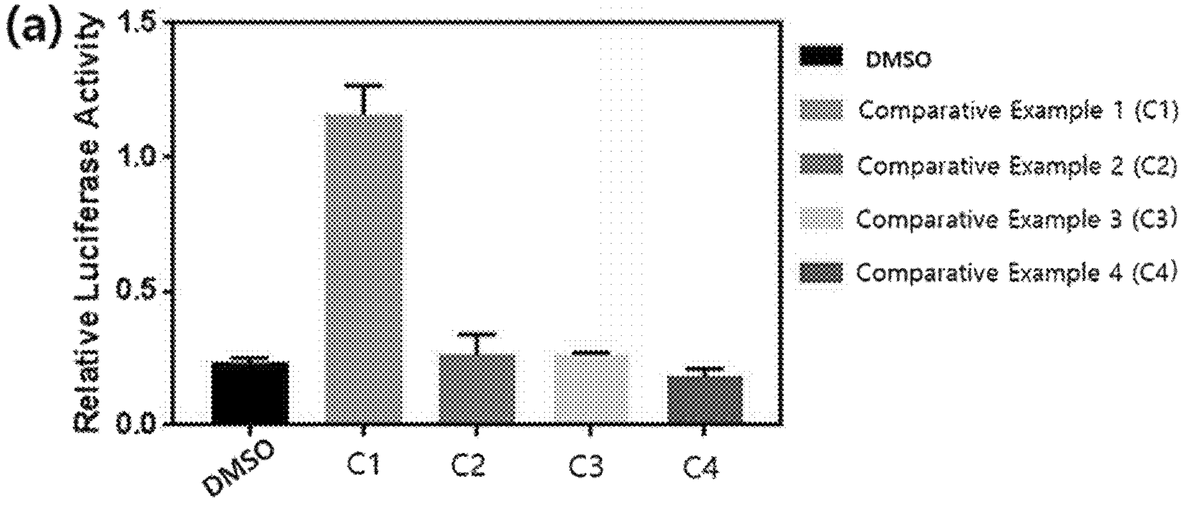
FIG. 1A illustrates the results of luciferase expression experiments using a reporter gene including a promoter from the start site of the human klotho gene of Comparative Examples 1 to 4 to the front of 1.7 kbp.

Hereinafter, the present invention will be described in detail.

The present invention relates to a composition for preventing or treating/improving chronic kidney disease (CKD), comprising a compound represented by Chemical Formula 1 or a pharmaceutically acceptable salt thereof as an active ingredient.

Chronic kidney disease (CKD) is defined as the presence of structural or functional abnormalities of the kidneys (e.g., proteinuria, hematuria, or pathological abnormalities), i.e., "kidney damage," for more than three months, or a decrease in glomerular filtration rate to 60 mL/min/1.73 $m^2$ or less for more than three months, with or without kidney damage, and is associated with various complications such as cardiovascular disease, mineral bone metabolism, and anemia, etc.

The compounds represented by Chemical Formula 1 below according to the present invention are effective in enhancing the expression of the Klotho gene, a gene associated with aging, and can be usefully used as a pharmaceutical composition or food composition for the prevention, amelioration or treatment of chronic kidney disease.

Pharmaceutical Composition for Preventing or Treating Chronic Kidney Disease (CKD)

The present invention provides a pharmaceutical composition for preventing or treating chronic kidney disease comprising a compound represented by Chemical Formula 1 below or a pharmaceutically acceptable salt thereof:

[Chemical Formula 1]

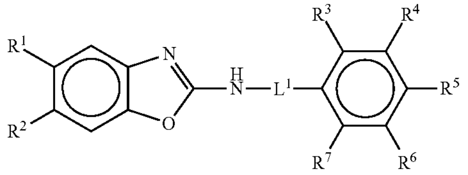

in Chemical Formula 1, $L^1$ is a single bond or

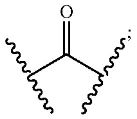 [SMILES: *C(*)=O]

$R^1$ and $R^2$ are each —H, —OH, a $C_{1-10}$ straight or branched alkyl, or a $C_{6-8}$ arylamide, wherein the aryl of the arylamide may be substituted with one or more of a halogen, $—NO_2$ and a $C_{1-10}$ straight or branched alkyl halide;

$R^1$ and $R^2$ may form a $C_{6-8}$ aryl with a carbon atom to which they are linked; and $R^3$, $R^4$, $R^5$, $R^6$ and $R^7$ may each be —H, a halogen, $—NO_2$ or a $C_{1-10}$ straight or branched alkyl.

In an exemplary embodiment according to the present invention, $L^1$ is a single bond or

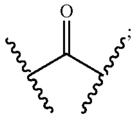

$R^1$ and $R^2$ are each —H, —OH, a $C_{1-5}$ straight or branched alkyl, or a $C_{6-7}$ arylamide, wherein the aryl of the arylamide may be substituted with one or more of a halogen, $—NO_2$ and a $C_{1-5}$ straight or branched alkyl halide;

$R^1$ and $R^2$ may form a $C_{6-7}$ aryl with a carbon atom to which they are linked; and $R^3$, $R^4$, $R^5$, $R^6$ and $R^7$ may each be —H, a halogen, $—NO_2$ or a $C_{1-5}$ straight or branched alkyl.

In an exemplary embodiment according to the present invention, $L^1$ is a single bond or

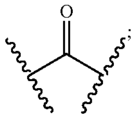 [SMILES: *C(*)=O]

$R^1$ and $R^2$ are each —H, —OH, $—CH_3$, or phenylamide, wherein the phenyl of the phenylamide may be substituted with one or more of —Cl, $—NO_2$ and $—CH_2Cl$;

$R^1$ and $R^2$ may form a phenyl with a carbon atom to which they are linked; and $R^3$, $R^4$, $R^5$, $R^6$ and $R^7$ may each be —H, —F, —Cl, $—NO_2$ or $—CH_2CH_3$.

In an exemplary embodiment according to the present invention, $L^1$ is a single bond or

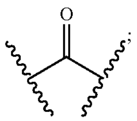 [SMILES: *C(*)=O]

$R^1$ is —H, —OH, —$CH_3$,

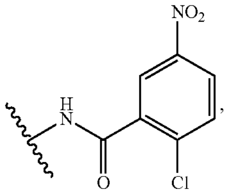

,

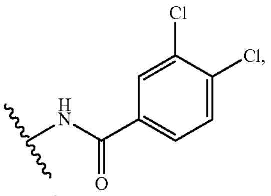

or

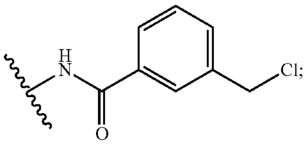

;

$R^2$ is —H;

$R^1$ and $R^2$ may form a phenyl with a carbon atom to which they are linked;

$R^3$ is —H or —Cl;

$R^4$ is —H, —F or —Cl;

$R^5$ is —F, —Cl, —$NO_2$, or —$CH_2CH_3$;

$R^6$ is —H; and $R^7$ may be —H.

Preferred example of the compound represented by Chemical Formula 1 according to the present invention may be the following compound group:

1) N-(benzo[d]oxazol-2-yl)-2-chloro-4-nitrobenzamide;
2) 8-methyl-2-[N-(3,4-dichlorophenyl)]aminobenzoxazole;
3) 2-((3,4-dichlorophenyl)amino)benzo[d]oxazol-5-ol;
4) N-(2-(4-ethylphenylamino)benzo[d]oxazol-5-yl)-2-chloro-5-nitrobenzamide;
5) N-(2-(4-ethylphenylamino)benzo[d]oxazol-5-yl)-3,4-dichlorobenzamide;
6) N-(2-(4-ethylphenylamino)benzo[d]oxazol-5-yl)-3-(chloromethyl)benzamide;
7) 2-[N-(3,4-dichlorophenyl)]aminobenzoxazole;
8) N-(3,4-dichlorophenyl)naphtho[2,3-d]oxazol-2-amine;
9) N-(3,4-difluorophenyl)-5-methylbenzo[d]oxazol-2-amine; or
10) N-(3,4-difluorophenyl)benzo[d]oxazol-2-amine.

In addition, in an exemplary embodiment according to the present invention, a compound represented by the following Chemical Formula 1-1 may be mentioned as a preferred embodiment of the compound represented by Chemical Formula 1.

[Formula 1-1]

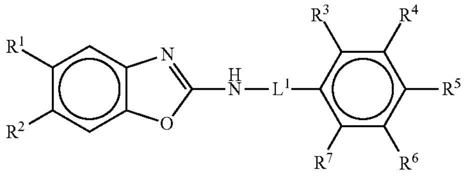

(In Chemical Formula 1-1, $L^1$ is a single bond;

$R^1$ and $R^2$ are each —H, or $C_{1-10}$ straight or branched chain alkyl;

$R^3$, $R^4$, $R^5$, $R^6$ and $R^7$ are each —H or halogen).

The compound represented by Chemical Formula 1 of the present invention can be used in the form of a pharmaceutically acceptable salt, and as a salt, an acid addition salt formed by a pharmaceutically acceptable free acid is useful. The expression "pharmaceutically acceptable salt" refers to any organic or inorganic addition salt of a base compound of Chemical Formula 1 whose concentration has effective action because it is relatively non-toxic and harmless to the patients and whose side effects resulting from the salt do not degrade the beneficial efficacy of the base compound of Chemical Formula 1. These salts may use an inorganic acid and an organic acid as a free acid, as the inorganic acid, it is possible to use hydrochloric acid, bromic acid, nitric acid, sulfuric acid, perchloric acid, phosphoric acid, and the like, and as the organic acid, it is possible to use citric acid, acetic acid, lactic acid, maleic acid, fumaric acid, gluconic acid, methanesulfonic acid, glycolic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, malonic acid, and the like. Further, these salts include alkali metal salts (sodium salts, potassium salts, and the like), alkaline earth metal salts (calcium salts, magnesium salts, and the like), and the like. For example, as an acid addition salt, acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salts, and the like may be included, and among them, hydrochloride or trifluoroacetate is preferred.

In addition, the compound represented by Chemical Formula 1 of the present invention includes not only pharmaceutically acceptable salts, but also all salts, isomers, hydrates and solvates that can be prepared by typical methods.

The addition salt according to the present invention may be prepared by a typical method, and may be prepared, for example, by dissolving the compound of Compound Formula 1 in a water-miscible organic solvent, for example, acetone, methanol, ethanol, or acetonitrile, or the like, adding an excessive amount of an organic acid thereto or adding an aqueous acid solution of an inorganic acid thereto, followed by precipitation or crystallization. Subsequently, the acid addition salt may be prepared by evaporating the solvent or excess acid from this mixture, and then drying the mixture or suction-filtering a precipitated salt.

Preparation Method 1 of the Compounds

The present invention can provide a method for preparing a compound represented by Chemical Formula 1A, as shown in the following Reaction Scheme 1, the method including:

obtaining Compound 4 by dissolving Compound 2 in an organic solvent, and then adding Compound 3 thereto, and reacting the resulting mixture at 10 to 50° C. for 12 to 20 hours (Step 1); and obtaining Compound 1A by adding an organic solvent in which Compound 4 obtained in Step 1 is dissolved dropwise to an organic solvent in which potassium superoxide is dissolved, and then reacting the resulting mixture at 15 to 30° C. for 10 to 16 hours (Step 2).

[Reaction Scheme 1]

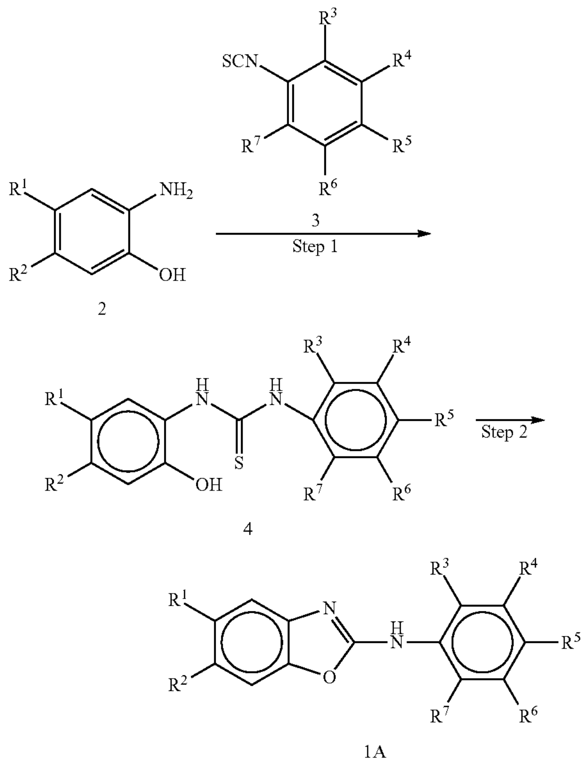

In Reaction Scheme 1, $R^1$, $R^2$, $R^3$, $R^4$, $R^5$, $R^6$ and $R^7$ are the same as defined in Chemical Formula 1 above, and Compound 1A is included in Chemical Formula 1 above.

In the preparation method of the present invention, as an example of the organic solvent, methanol (MeOH), dimethylformamide (DMF), acetonitrile (MeCN), tetrahydrofuran (THF), dichloromethane (DCM), 1,2-dimethoxyethane, benzene, toluene, xylene, dimethyl sulfoxide (DMSO), or dioxane may be used alone or in mixtures thereof.

In the preparation method of the present invention, an example of the compound that can be prepared by the above preparation method may be 8-methyl-2-[N-(3,4-dichlorophenyl)]aminobenzoxazole, 2-[N-(3,4-dichlorophenyl)]aminobenzoxazole, N-(3,4-dichlorophenyl)naphtho[2,3-d]oxazol-2-amine, N-(3,4-difluorophenyl)-5-methylbenzo[d]oxazol-2-amine or N-(3,4-difluorophenyl)benzo[d]oxazol-2-amine.

Preparation Method 2 of the Compounds

The present invention can provide a method for preparing a compound represented by Chemical Formula 1B, as shown in the following Reaction Scheme 2, the method including:

obtaining Compound 6 by dissolving Compound 5 in an organic solvent, and then adding Compound 3 thereto, and reacting the resulting mixture at 10 to 50° C. for 12 to 20 hours (Step 1);

obtaining Compound 7 by adding an organic solvent in which Compound 6 obtained in Step 1 is dissolved dropwise to an organic solvent in which potassium superoxide is dissolved, and then reacting the resulting mixture for 12 to 24 hours (Step 2); and obtaining Compound 1B by dissolving Compound 7 in an organic solvent, adding boron tribromide ($BBr_3$) thereto, and then reacting the resulting mixture at room temperature for 20 to 28 hours (Step 3).

[Reaction Scheme 2]

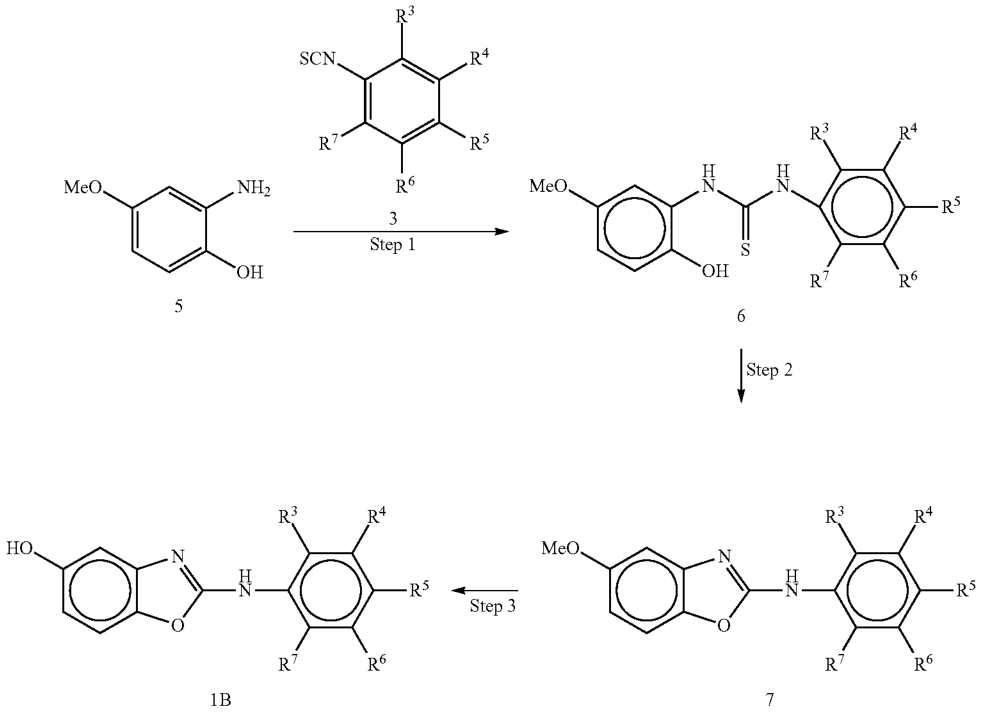

In Reaction Scheme 2, $R^3$, $R^4$, $R^5$, $R^6$ and $R^7$ are the same as defined in Chemical Formula 1 above, and Compound 1B is included in Chemical Formula 1 above.

In the preparation method of the present invention, as an example of the organic solvent, methanol (MeOH), dimethylformamide (DMF), acetonitrile (MeCN), tetrahydrofuran (THF), dichloromethane (DCM), 1,2-dimethoxyethane, benzene, toluene, xylene, dimethyl sulfoxide (DMSO), or dioxane may be used alone or in combination.

In the preparation method of the present invention, an example of the compound that can be prepared by the above preparation method may be 2-((3,4-dichlorophenyl)amino) benzo[d]oxazol-5-ol.

Preparation Method 3 of the Compounds

The present invention provides a method for preparing a compound represented by Chemical Formula 1C, as shown in the following Reaction Scheme 3, the method including:

obtaining Compound 9 by dissolving Compound 8, carbon disulfide, iodomethane and sodium hydride in an organic solvent, and then reacting the resulting solution at 10 to 50° C. for 2 to 8 hours (Step 1); and obtaining Compound 1C by dissolving Compound 9 and Compound 2 in an organic solvent, and then reacting the resulting solution for 2 to 8 hours (Step 2).

[Reaction Scheme 3]

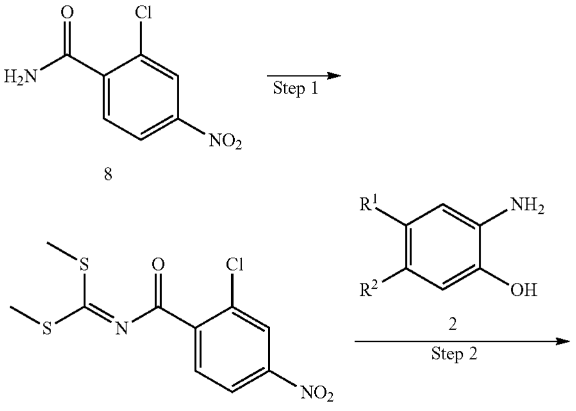

8

2

9

-continued

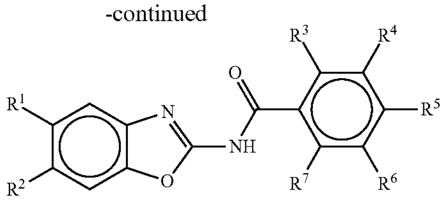

1C

In Reaction Scheme 3, $R^1$, $R^2$, $R^3$, $R^4$, $R^5$, $R^6$ and $R^7$ are the same as defined in Chemical Formula 1 above, and Compound 1C is included in Chemical Formula 1 above.

In the preparation method of the present invention, as an example of the organic solvent, methanol (MeOH), dimethylformamide (DMF), acetonitrile (MeCN), tetrahydrofuran (THF), dichloromethane (DCM), 1,2-dimethoxyethane, benzene, toluene, xylene, dimethyl sulfoxide (DMSO), or dioxane may be used alone or in combination.

In the preparation method of the present invention, an example of the compound that can be prepared by the above preparation method may be N-(benzo[d]oxazol-2-yl)-2-chloro-4-nitrobenzamide.

Preparation Method 4 of the Compounds

The present invention provides a method for preparing a compound represented by Chemical Formula 1D, as shown in the following Reaction Scheme 4, the method including:

obtaining Compound 11 by dissolving Compound 10 and Compound 3 in an organic solvent, and then reacting the resulting solution at 10 to 50° C. for 20 to 28 hours (Step 1);

obtaining Compound 12 by adding an organic solvent in which Compound 11 obtained in Step 1 is dissolved dropwise to an organic solvent in which potassium superoxide is dissolved, and then reacting the resulting mixture at 10 to 50° C. for 12 to 24 hours (Step 2);

obtaining Compound 13 by adding Compound 12 together with a catalyst to an organic solvent, and then injecting hydrogen gas thereinto, and reacting the resulting mixture at 10 to 50° C. for 12 to 20 hours (Step 3); and obtaining Compound 1D by dissolving Compound 13 and Compound 14 in an organic solvent, and then reacting the resulting solution at 10 to 50° C. for 12 to 24 hours (Step 4).

[Reaction Scheme 4]

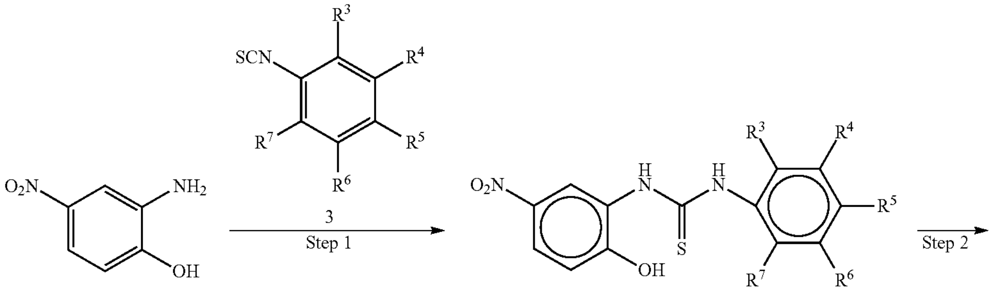

3

10

11

-continued

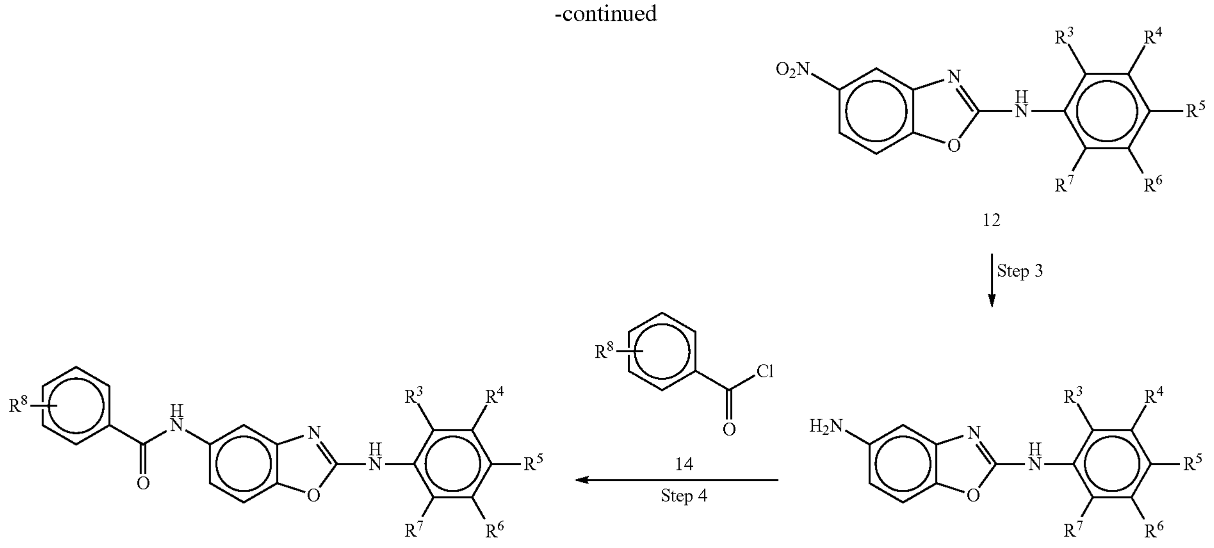

12

13

1D

In Reaction Scheme 4, $R^3$, $R^4$, $R^5$, $R^6$ and $R^7$ are the same as defined in Chemical Formula 1 of claim 1;

$R^8$ is one or more of a halogen, —$NO_2$ and a $C_{1-10}$ straight or branched alkyl halide; and Compound 1D is included in Chemical Formula 1 of claim 1.

In the preparation method of the present invention, as an example of the organic solvent, methanol (MeOH), dimethylformamide (DMF), acetonitrile (MeCN), tetrahydrofuran (THF), dichloromethane (DCM), 1,2-dimethoxyethane, benzene, toluene, xylene, dimethyl sulfoxide (DMSO), or dioxane may be used alone or in combination.

In the preparation method of the present invention, an example of the compound that can be prepared by the above preparation method may be N-(2-(4-ethylphenylamino) benzo[d]oxazol-5-yl)-2-chloro-5-nitrobenzamide, N-(2-(4-ethylphenylamino)benzo[d]oxazol-5-yl)-3,4-dichlorobenzamide or N-(2-(4-ethylphenylamino)benzo [d]oxazol-5-yl)-3-(chloromethyl)benzamide.

In the present invention, the present composition can improve the expression level of Klotho gene.

In the present invention, the chronic kidney disease may be defined as a disease state in which there is kidney damage or decreased kidney function lasting more than three months. Specifically, the chronic kidney disease may include, but is not limited to, one or more diseases selected from the group consisting of chronic nephritis, chronic pyelonephritis, nephrotic syndrome, chronic pyelonephritis, urinary tract infection, diabetic nephropathy, chronic glomerulonephritis, nephroze syndrome, microglomerular sclerosis, membranous nephropathy, and membranoproliferative glomerulonephritis.

The compound of the present invention may be administered in various oral and parenteral dosage forms, and during the formulation, the compound of the present invention is prepared using a diluent or an excipient, such as a filler, a thickener, a binder, a wetting agent, a disintegrant, and a surfactant which are commonly used.

A solid formulation for oral administration includes a tablet, a pill, a powder, a granule, a capsule, a troche, and the like, and the solid formulation is prepared by mixing at least one excipient, for example, a starch, calcium carbonate, sucrose or lactose, gelatin, and the like with one or more compounds of the present invention. Further, in addition to a simple excipient, lubricants such as magnesium stearate and talc are also used. A liquid preparation for oral administration corresponds to a suspension agent, a liquid for internal use, an emulsion, a syrup, and the like, and the liquid preparation may include various excipients, for example, a wetting agent, a sweetener, an aroma, a preservative, and the like, in addition to water and liquid paraffin which are commonly used simple diluents.

A preparation for parenteral administration includes an aqueous sterile solution, a non-aqueous solvent, a suspension solvent, an emulsion, a freeze-dried preparation, a suppository, or the like. As a non-aqueous solvent and a suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerol, gelatin, and the like.

In addition, the effective dosage of the compound of the present invention to the human body may vary depending on the patient's age, body weight, sex, administration form, health condition, and severity of disease, and is generally about 0.001 to 100 mg/kg/day, preferably 0.01 to 35 mg/kg/day. Based on an adult patient weighing 70 kg, the dosage is generally 0.07 to 7,000 mg/day, preferably 0.7 to 2,500 mg/day, and the compound of the present invention may be administered in divided doses once or several times a day at regular time intervals according to the judgment of a doctor or pharmacist.

Food Composition or Health Functional Food Composition for Preventing or Improving Chronic Kidney Disease The present invention provides a food composition or a health functional food composition for preventing or improving chronic kidney disease comprising the compound represented by Chemical Formula 1 or a pharmaceutically acceptable salt thereof.

In the present invention, the composition can improve the expression level of Klotho gene.

In the present invention, the chronic kidney disease may be defined as a disease state in which there is kidney damage or decreased kidney function lasting more than three months. Specifically, the chronic kidney disease may include, but is not limited to, one or more diseases selected from the group consisting of chronic nephritis, chronic pyelonephritis, nephrotic syndrome, chronic pyelonephritis, urinary tract infection, diabetic nephropathy, chronic glomerulonephritis, nephroze syndrome, microglomerular sclerosis, membranous nephropathy, and membranoproliferative glomerulonephritis.

The type of food is not particularly limited. Examples of foods to which the active material of the present invention can be added include drinks, meats, sausages, bread, biscuits, rice cakes, chocolate, candies, snacks, confectioneries, pizza, instant noodles, other noodles, gums, dairy products including ice cream, various soups, drinking water, alcoholic beverages, vitamin complexes, milk products, dairy products, and the like, and include all health foods and health functional foods in a typical sense.

The health food and health functional food composition containing the active material according to the present invention may be added to food as it is or may be used together with other foods or food ingredients, and may be appropriately used according to a typical method. The mixing amount of the active material may be suitably determined depending on the purpose of use (for prevention or alleviation). In general, the amount of the composition in health foods and health functional foods may be 0.1 to 90 parts by weight of the total food weight. However, in the case of long-term intake for the purpose of maintaining health or for the purpose of health control, the amount may be equal to or less than the above range, and the effective material may be used in an amount equal to or more than the above range because it poses no problem in terms of safety.

Other ingredients are not particularly limited, other than that the health food and health functional food composition of the present invention contains the active material of the present invention as an essential ingredient at an indicated ratio, and the health food and health functional food composition of the present invention may contain various flavoring agents like those of a typical beverage, natural carbohydrates, and the like as additional ingredients. Examples of the above-described natural carbohydrates include typical sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As flavoring agents in addition to those described above, a natural flavoring agent (thaumatin), a stevia extract (for example, rebaudioside A, glycyrrhizin and the like), and a synthetic flavoring agent (saccharin, aspartame and the like) may be advantageously used. The proportion of the natural carbohydrate is generally about 1 to 20 g, and preferably about 5 to 12 g per 100 g of the health functional food composition of the present invention.

The health food and health functional food composition containing the active material of the present invention may contain various nutrients, vitamins, minerals (electrolytes), flavoring agents such as synthetic flavoring agents and natural flavoring agents, colorants and thickening agents (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in carbonated beverages, or the like, in addition to the additives. In addition, the health food and health functional food composition of the present invention may contain flesh for preparing natural fruit juice, fruit juice drinks, and vegetable drinks.

These ingredients may be used either independently or in combination. The proportion of these additives is not particularly important, but is generally selected within a range of 0.1 to 20 parts by weight per 100 parts by weight of the health food and health functional food composition of the present invention containing the active material of the present invention.

Hereinafter, the present invention will be described in more detail with reference to the following examples. However, the following examples are only for exemplifying the present invention, and the content of the present invention is not limited by the following examples.

<Example 1> Preparation of N-(benzo[d]oxazol-2-yl)-2-chloro-4-nitrobenzamide (FCCS-17064)

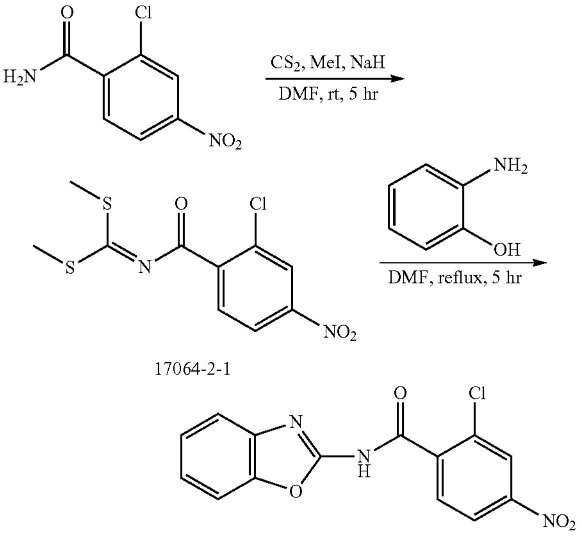

17064-2-1

FCCS-17064

Step 1: Preparation of dimethyl(2-chloro-4-nitrobenzoyl)carbonimidodithioate (17064-2-1)

After 2-chloro-4-nitrobenzamide (500 mg, 2.49 mmol), carbon disulfide ($CS_2$) (759 mg, 9.97 mmol), and iodomethane (1.13 g, 7.97 mmol) were dissolved in N,N-dimethylformamide (7 mL), 60% sodium hydride (200 mg, 4.98 mmol) was added thereto, and the resulting mixture was stirred at room temperature for 5 hours.

Ice-cold water was slowly added to the reaction mixture, and the mixture was extracted with ethyl acetate. The organic layer was washed with brine and dried over $Na_2SO_4$, and then the solvent was removed under reduced pressure. The reaction mixture was purified by silica-gel column chromatography (10% ethyl acetate/n-hexane) to obtain dimethyl(2-chloro-4-nitrobenzoyl)carbonimidodithioate (17064-2-1) as a light yellow solid (160 mg, 21%).

$^1$H NMR (400 MHz, acetone-$d_6$); δ8.34 (d, 1H, J=2.0 Hz), 8.29 (dd, 1H, J=2.4, 8.8 Hz), 8.20 (d, 1H, J=8.4 Hz), 2.65 (s, 6H).

Step 2: Preparation of N-(benzo[d]oxazol-2-yl)-2-chloro-4-nitrobenzamide (FCCS-17064)

After the dimethyl(2-chloro-4-nitrobenzoyl)carbonimidodithioate (17064-2-1) (150 mg, 0.49 mmol) obtained in Step 1 was dissolved in N,N-dimethylformamide (15 mL), 2-aminophenol (53 mg, 0.49 mmol) was added thereto.

After the reaction mixture was refluxed for 6 hours, the solvent was removed under reduced pressure. A solid obtained by adding diethyl ether to the reaction mixture and filtering a precipitated solid was purified by silica-gel column chromatography (40% ethyl acetate/n-hexane) to obtain a target compound N-(benzo[d]oxazol-2-yl)-2-chloro-4-nitrobenzamide (FCCS-17064) as a brown solid (70 mg, 30%).

$^1$H NMR (400 MHz, acetone-$d_6$); δ8.36 (d, 1H, J=2.0 Hz), 8.33 (dd, 1H, J=2.0, 8.4 Hz), 8.09 (d, 1H, J=8.4 Hz), 7.62-7.56 (m, 2H), 7.40-7.33 (m, 2H).

<Example 2> Preparation of 8-methyl-2-[N-(3,4-dichlorophenyl)]aminobenzoxazole (FCCS-17065)

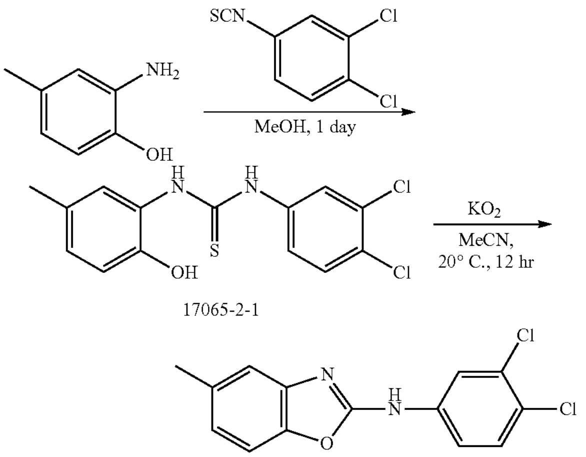

17065-2-1

FCCS-17065

Step 1: Preparation of 1-(3,4-dichlorophenyl)-3-(2-hydroxy-5-methylphenyl)thiourea (17065-2-1)

After 2-amino-p-cresol (300 mg, 2.44 mmol) was dissolved in methanol (12 mL), 3,4-dichlolrophenyl isothiocyanate (497 mg, 2.44 mmol) was added thereto, and the resulting mixture was stirred at room temperature for 18 hours. After the termination of the reaction was confirmed by thin layer chromatography (TLC), the resulting product was cooled in a refrigerator (0 to 4° C.). 1-(3,4-Dichlorophenyl)-3-(2-hydroxy-5-methylphenyl)thiourea (17065-2-1) as a white solid (346 mg) was obtained by filtering a precipitated solid, and was used in the next step without further purification.

$^1$H NMR (400 MHz, acetone-$d_6$); δ7.98 (dd, 1H, J=0.4, 2.0 Hz), 7.55-7.50 (m, 2H), 7.43 (br s, 1H), 6.94-6.90 (m, 1H), 6.85 (d, 1H, J=8.4 Hz) 2.24 (s, 3H).

Step 2: Preparation of 8-methyl-2-[N-(3,4-dichlorophenyl)]aminobenzoxazole (FCCS-17065)

After the 1-(3,4-dichlorophenyl)-3-(2-hydroxy-5-methylphenyl)thiourea (17065-2-1) (346 mg, 1.06 mmol) obtained in Step 1 in a solution of potassium superoxide ($KO_2$) (375 mg, 5.29 mmol) and acetonitrile (MeCN) (15 mL) was slowly added to a solution dissolved in acetonitrile (MeCN) (25 mL), the resulting mixture was stirred at room temperature for 18 hours.

Dichloromethane and water were added to the reaction mixture, and the mixture was extracted. The organic layer was washed with brine and dried over $Na_2SO_4$, and then the solvent was removed under reduced pressure. The reaction mixture was purified by silica-gel column chromatography (10% ethyl acetate/n-hexane to obtain a target compound 8-methyl-2-[N-(3,4-dichlorophenyl)]aminobenzoxazole (FCCS-17065) as a white solid (170 mg, 24%, 2 steps).

$^1$H NMR (400 MHz, acetone-$d_6$); δ8.29 (d, 1H, J=2.8 Hz), 7.73 (dd, 1H, J=2.8, 8.8 Hz), 7.76 (d, 1H, J=8.8 Hz), 7.32-7.20 (m, 1H), 7.28 (d, 1H, J=8.0 Hz), 7.00-6.970 (m, 1H), 2.41 (s, 3H).

<Example 3> Preparation of 2-((3,4-dichlorophenyl)amino)benzo[d]oxazol-5-ol (FCCS-17066)

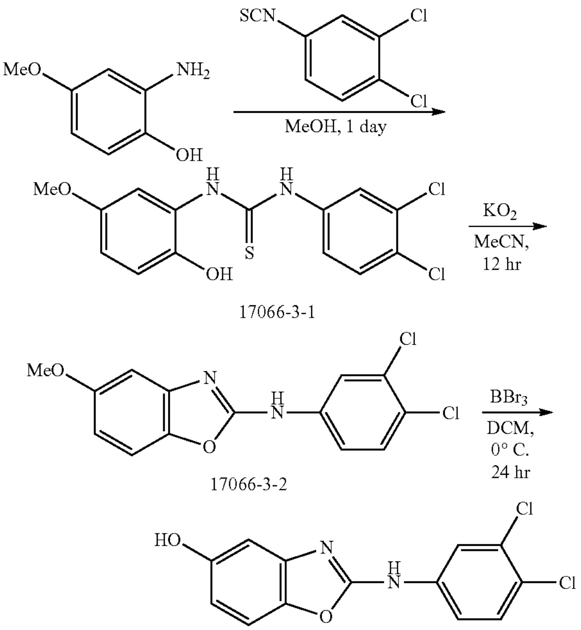

17066-3-1

17066-3-2

FCCS-17066

Step 1: Preparation of 1-(3,4-dichlorophenyl)-3-(2-hydroxy-5-methoxyphenyl)thiourea (17066-3-1)

After 2-amino-4-methoxyphenol (1.13 g, 8.12 mmol) was dissolved in methanol (40 mL), 3,4-dichlolrophenyl isothiocyanate (1.99 g, 9.74 mmol) was added thereto, and the resulting mixture was stirred at room temperature for 18 hours. After the end of the reaction was confirmed by thin layer chromatography (TLC), the resulting product was cooled in a refrigerator (0 to 4° C.). 1-(3,4-Dichlorophenyl)-3-(2-hydroxy-5-methylphenyl)thiourea (17066-3-1) as a brown solid (2 g) was obtained by filtering a precipitated solid, and was used in the next step without further purification.

$^1$H NMR (400 MHz, methanol-$d_4$); δ7.82 (d, 1H, J=2.4 Hz), 7.48-7.44 (m, 2H), 7.39 (dd, 1H, J=1.4, 8.8 Hz), 6.81 (d, 1H, J=8.8 Hz), 6.66 (dd, 1H, J=1.6, 8.8 Hz), 3.73 (s, 3H).

Step 2: Preparation of N-(3,4-dichlorophenyl)-5-methoxybenzo[d]oxazol-2-amine (17066-3-2)

After the 17066-3-1 (525 mg, 1.52 mmol) obtained in Step 1 in a solution of potassium superoxide ($KO_2$) (540 mg, 7.6 mmol) and acetonitrile (MeCN) (20 mL) was slowly added to a solution dissolved in acetonitrile (MeCN) (30 mL), the resulting mixture was stirred at room temperature for 18 hours. Dichloromethane and water were added to the reaction mixture, and the mixture was extracted. The organic layer was washed with brine and dried over $Na_2SO_4$, and then the solvent was removed under reduced pressure. The reaction mixture was purified by silica-gel column chromatography (20% ethyl acetate/n-hexane) to obtain N-(3,4-dichlorophenyl)-5-methoxybenzo[d]oxazol-2-amine (17066-3-2) as a brown solid (230 mg, 35%).

$^1$H NMR (400 MHz, acetone-$d_6$); δ8.29 (d, 1H, J=2.4 Hz), 7.70 (dd, 1H, J=2.4, 8.8 Hz), 7.55 (d, 1H, J=8.8 Hz), 7.30 (d, 1H, J=8.8 Hz), 7.08 (d, 1H, J=2.8 Hz), 7.74 (dd, 1H, J=2.4, 8.8 Hz), 3.84 (s, 3H).

Step 3: Preparation of 2-((3,4-dichlorophenyl)amino)benzo[d]oxazol-5-ol (FCCS-17066)

After the 17066-3-2 (200 mg, 0.65 mmol) obtained in Step 2 was dissolved in dichloromethane (15 mL, anhydrous) in an Ar gas atmosphere, the resulting solution was cooled in an ice bath. Boron tribromide ($BBr_3$) (3.23 mL, 1.0 M in dichloromethane) was slowly added thereto, the temperature was increased to room temperature, and then the resulting mixture was stirred for 24 hours. The reaction was terminated by slowly adding a sodium hydroxide (NaOH) solution (8 mL, 1.0 M in water) thereto and the resulting product was transferred to a separatory funnel to separate an organic layer and an aqueous layer. The aqueous layer was extracted with ethyl acetate, and then dried over $Na_2SO_4$, and then the solvent was removed under reduced pressure. The reaction mixture was purified by silica-gel column chromatography (40% ethyl acetate/n-hexane) to obtain a target compound 2-((3,4-dichlorophenyl)amino)benzo[d]oxazol-5-ol (FCCS-17066) as a brown solid (97 mg, 50%).

$^1$H NMR (400 MHz, acetone-$d_6$); δ8.29 (br s, —OH), 8.26 (d, 1H, J=2.4 Hz), 7.72 (dd, 1H, J=2.4, 8.8 Hz), 7.56 (d, 1H, J=8.8 Hz), 7.21 (dd, 1H, J=2.0, 7.2 Hz), 6.95 (d, 1H, J=2.0 Hz), 6.66 (dd, 1H, J=2.4, 8.8 Hz).

<Example 4> Preparation of N-(2-(4-ethylphenylamino)benzo[d]oxazol-5-yl)-2-chloro-5-nitrobenzamide (FCCS-17067)

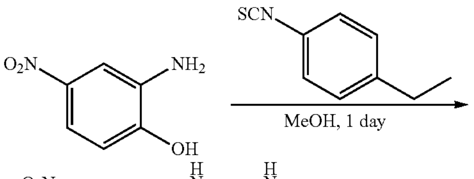

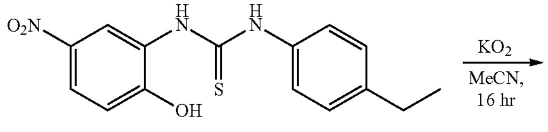

Interm-3-1

-continued

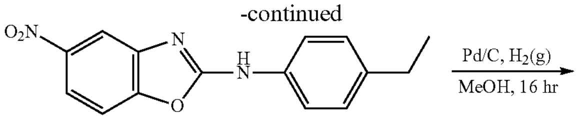

Interm-3-2

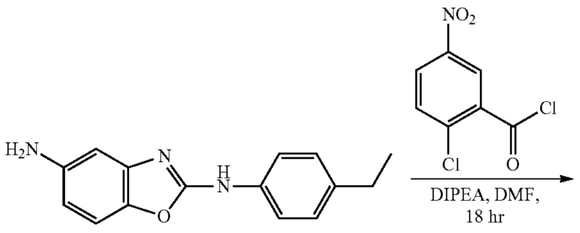

Interm-3-3

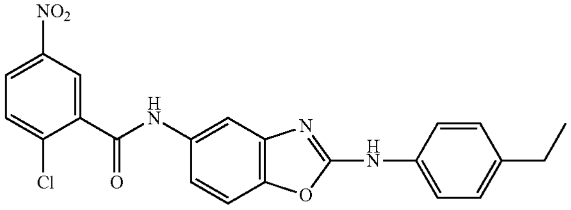

FCCS-17067

Step 1: Preparation of 1-(4-ethylphenyl)-3-(2-hydroxy-5-nitrophenyl)thiourea (Interm-3-1)

After 2-amino-4-nitrophenol (1.88 g, 12.25 mmol) and 4-ethylphenyl isothiocyanate (2 g, 12.25 mmol) were dissolved in methanol (80 mL), the resulting solution was stirred at room temperature overnight. After the solvent was removed under reduced pressure, the residue was purified by silica-gel column chromatography (20% ethyl acetate/n-hexane) to obtain 1-(4-ethylphenyl)-3-(2-hydroxy-5-nitrophenyl)thiourea (Interm-3-1) as a brown solid (2.9 g, 65%).

$^1$H NMR (400 MHz, methanol-$d_4$); δ9.24 (d, 1H, J=2.8 Hz), 7.88 (dd, 1H, J=2.0, 9.2 Hz), 7.36 (d, 2H, J=8.4 Hz), 7.25 (d, 2H, J=8.8 Hz), 6.94 (d, 1H, J=9.2 Hz), 2.66 (q, 2H, J=7.6 Hz), 1.24 (t, 3H, J=7.6 Hz).

Step 2: Preparation of N-(4-ethylphenyl)-5-nitrobenzo[d]oxazol-2-amine (Interm-3-2)

After a solution of potassium superoxide ($KO_2$) (2.8 g, 39.38 mmol) and acetonitrile (MeCN) (130 mL) was cooled in an ice bath, a solution of the Interm-3-1 (2.5 g, 7.88 mmol) obtained in Step 1 dissolved in acetonitrile (MeCN) (170 mL) was slowly added thereto, and then the resulting solution was stirred at room temperature for 18 hours. Dichloromethane and water were added to the reaction mixture, and the mixture was extracted. The organic layer was washed with brine and dried over $Na_2SO_4$, and then the solvent was removed under reduced pressure. The reaction mixture was purified by silica-gel column chromatography (10% ethyl acetate/n-hexane) to obtain Compound Interm-3-2 as a brown solid (1.78 g, 80%).

$^1$H NMR (400 MHz, methanol-$d_4$); δ8.20 (d, 1H, J=1.0 Hz), 8.08 (dd, 1H, J=0.8, 9.6 Hz), 7.59 (d, 2H, J=8.8 Hz), 7.51 (d, 1H, J=8.8 Hz), 7.22 (d, 2H, J=8.8 Hz), 2.64 (q, 2H, J=7.6 Hz), 1.24 (t, 3H, J=7.6 Hz).

Step 3: Preparation of N-(4-ethylphenyl)benzo[d]oxazole-2,5-diamine (Interm-3-3)

After palladium on carbon (Pd/C) (1.70 g, 0.80 mmol, 10 wt %, wet support) was weighed and put into a roundbottom flask, the flask was purged with Ar gas. After a solution of the Interm-3-2 (1.58 g, 5.30 mmol) obtained in Step 2 dissolved in methanol (80 mL) was slowly added thereto, the atmosphere in the flask was substituted with $H_2(g)$. The solution was stirred at room temperature for 18 hours while bubbling $H_2(g)$. After the termination of the reaction was confirmed by thin layer chromatography (TLC), the resulting product was filtered with a Celite pad, and then the solvent was removed under reduced pressure. The reaction mixture was purified by silica-gel column chromatography (40% ethyl acetate/n-hexane) to obtain Compound Interm-3-3 as a light brown solid (1.21 g, 90%).

$^1H$ NMR (400 MHz, Acetone-$d_6$); δ7.71 (m, 2H), 7.19 (m, 2H), 7.03 (dd, 1H, J=0.8, 8.4 Hz), 6.75 (dd, 1H, J=0.8, 2.0 Hz), 6.44 (dd, 1H, J=2.0, 8.4 Hz), 2.60 (q, 2H, J=7.6 Hz), 1.19 (t, 3H, J=7.6 Hz).

Step 4: Preparation of N-(2-(4-ethylphenylamino)benzo[d]oxazol-5-yl)-2-chloro-5-nitrobenzamide (FCCS-17067)

After the Interm-3-3 (253 mg, 1 mmol) obtained in Step 3 and 2-chloro-5-nitrobenzoyl chloride (220 mg, 1 mmol) were dissolved in N,N-dimethylformamide (DMF) (4 mL), diisopropylethylamine (DIPEA) (129 mg, 1 mmol) was added thereto, and the resulting mixture was stirred at room temperature for 18 hours. After 18 hours, 0.5 equiv. of each of 2-chloro-5-nitrobenzoyl chloride and diisopropylethylamine (DIPEA) was added thereto, and the resulting mixture was further stirred for 8 hours. 10% HCl (aq.) was added to the reaction mixture, the mixture was extracted with ethyl acetate, and then the organic layer was sequentially washed with a saturated aqueous $NaHCO_3$ solution and brine. After the organic layer was dried over $Na_2SO_4$, the solvent was removed under reduced pressure. The reaction mixture was purified by silica-gel column chromatography (40% ethyl acetate/n-hexane) to obtain a target compound N-(2-(4-ethylphenylamino)benzo[d]oxazol-5-yl)-2-chloro-5-nitrobenzamide (FCCS-17067) as a light yellow solid (120 mg, 27%).

$^1H$ NMR (400 MHz, DMSO-$d_6$); δ 10.71 (s, 1H), 10.53 (s, 1H), 8.48 (d, 1H, J=2.8 Hz), 8.34 (dd, 1H, J=2.4, 8.8 Hz), 7.90 (d, 1H, J=8.8 Hz), 7.82 (d, 1H, J=2.0 Hz), 7.64 (d, 2H, J=8.8 Hz), 7.46 (d, 1H, J=8.8 Hz), 7.40 (dd, 1H, J=2.0, 8.4 Hz), 7.21 (d, 1H, J=8.8 Hz), 2.58 (q, 2H, J=7.6 Hz), 1.18 (t, 3H, J=7.6 Hz).

<Example 5> Preparation of N-(2-(4-ethylphenylamino)benzo[d]oxazol-5-yl)-3,4-dichlorobenzamide (FCCS-17068)

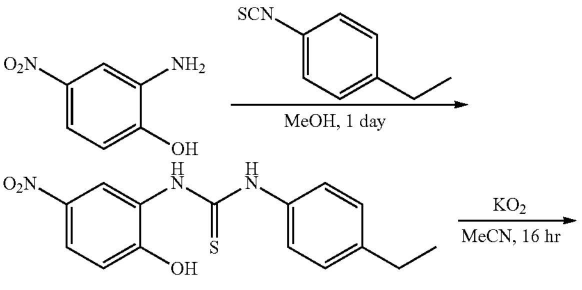

Interm-3-1

-continued

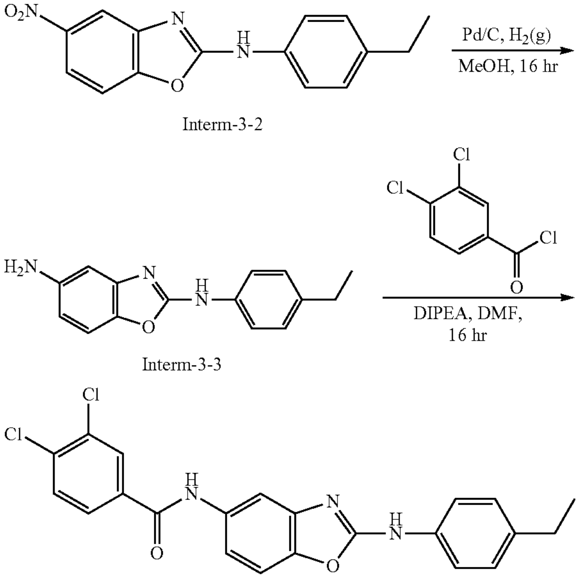

Interm-3-2

Interm-3-3

FCCS-17068

After the Interm-3-3 (253 mg, 1 mmol) obtained in Step 3 in Example 4 and 3,4-dichlorobenzoyl chloride (209 mg, 1 mmol) were dissolved in N,N-dimethylformamide (DMF) (4 mL), diisopropylethylamine (DIPEA) (129 mg, 1 mmol) was added thereto, and the resulting mixture was stirred at room temperature for 18 hours. 10% HCl (aq.) was added to the reaction mixture, the mixture was extracted with ethyl acetate, and then the organic layer was sequentially washed with a saturated aqueous $NaHCO_3$ solution and brine. After the organic layer was dried over $Na_2SO_4$, the solvent was removed under reduced pressure. The reaction mixture was purified by silica-gel column chromatography (40% ethyl acetate/n-hexane) to obtain a target compound FCCS-17067 as a light white solid (270 mg, 64%).

$^1H$ NMR (400 MHz, Acetone-$d_6$); δ8.18 (d, 1H, J=2.4 Hz), 7.99 (t, 1H, J=2.4 Hz), 7.97 (d, 1H, J=2.0 Hz), 7.80-7.20 (m, 3H), 7.70-7.50 (m, 1H), 7.35 (d, 1H, J=8.8 Hz), 7.24 (d, 1H, J=8.8 Hz), 2.63 (q, 2H, J=7.6 Hz), 1.22 (t, 3H, J=7.6 Hz).

<Example 6> Preparation of N-(2-(4-ethylphenylamino)benzo[d]oxazol-5-yl)-3-(chloromethyl)benzamide (FCCS-17069)

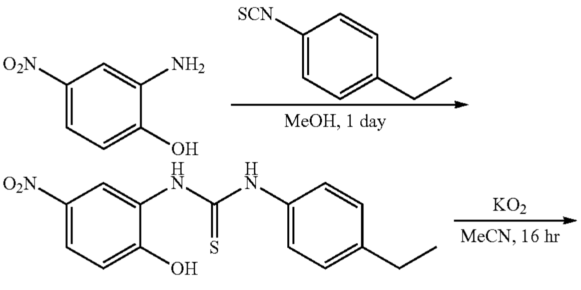

Interm-3-1

-continued

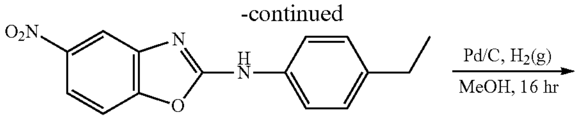

Interm-3-2

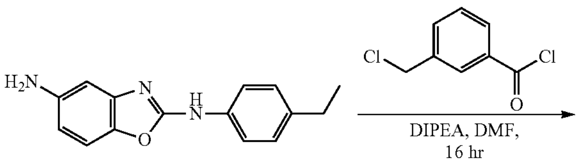

Interm-3-3

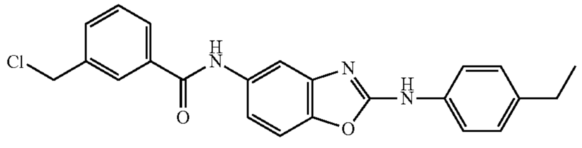

FCCS-17069

After the Interm-3-3 (253 mg, 1 mmol) obtained in Step 3 in Example 4 and 3-(chloromethyl)benzoyl chloride (189 mg, 1 mmol) were dissolved in N,N-dimethylformamide (DMF) (4 mL), diisopropylethylamine (DIPEA) (129 mg, 1 mmol) was added thereto, and the resulting mixture was stirred at room temperature for 18 hours. 10% HCl (aq.) was added to the reaction mixture, the mixture was extracted with ethyl acetate, and then the organic layer was sequentially washed with a saturated aqueous solution of $NaHCO_3$ and brine. After the organic layer was dried over $Na_2SO_4$, the solvent was removed under reduced pressure. The reaction mixture was purified by silica-gel column chromatography (30% ethyl acetate/n-hexane) to obtain a target compound FCCS-17067 as a pale white solid (170 mg, 40%).

$^1$H NMR (400 MHz, Acetone-$d_6$); δ8.08 (t, 1H, J=1.2 Hz), 8.03 (d, 1H, J=2.0 Hz), 7.98 (dt, 1H, J=1.2, 7.6 Hz), 7.80-7.75 (m, 2H), 7.69-7.65 (m, 1H), 7.57-7.52 (m, 3H), 7.34 (d, 1H, J=8.8 Hz), 7.26-7.22 (m, 2H), 2.62 (q, 2H, J=7.6 Hz), 1.22 (t, 3H, J=7.6 Hz).

<Example 7> Preparation of 2-[N-(3,4-dichlorophenyl)]aminobenzoxazole (FCCS-17065-A)

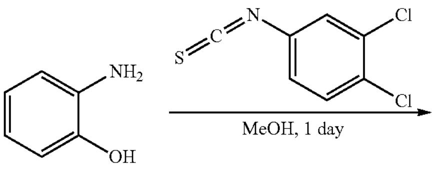

2-aminophenol

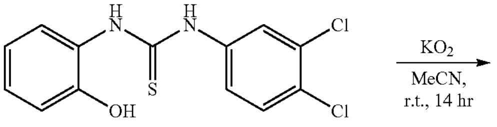

FCCS-17065-A-2-1

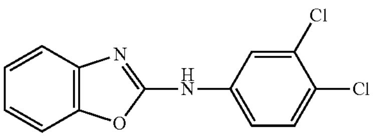

FCCS-17065-A

Step 1: Preparation of 1-(3,4-dichlorophenyl)-3-(2-hydroxyphenyl)thiourea (FCCS-17065-A-2-1)

After methanol (anhydrous MeOH) (8 mL) was added to and dissolved in 2-aminophenol (300 mg, 2.749 mmol) in an Ar gas atmosphere, 3,4-dichlorophenyl isothiocyanate (0.47 mL, 3.299 mmol) was slowly added dropwise thereto and the resulting mixture was stirred at room temperature for 14 hours. It was confirmed by thin layer chromatography (TLC) that all starting materials had disappeared, the solvent was removed by reducing pressure, and then silica was added to and adsorbed to a crude product, and silica-gel flash column chromatography (30% EtOAc/hexane, $R_f$=0.4) was performed to obtain 793 mg (light brown foamy solid, 92%) of 1-(3,4-dichlorophenyl)-3-(2-hydroxyphenyl)thiourea (FCCS-17065-A-2-1).

$^1$H NMR (400 MHz, CD3OD); δ7.82 (d, 1H, J=2.8 Hz), 7.63 (d, 1H, J=7.6 Hz), 7.45 (d, 1H, J=8.8 Hz), 7.39 (dd, 1H, J=8.6, 2.2 Hz), 7.11-7.06 (m, 1H), 6.90 (dd, 1H, J=8.0, 1.2 Hz), 6.85 (td, 1H, J=7.6, 1.2 Hz)

Step 2: Preparation of 2-[N-(3,4-dichlorophenyl)]aminobenzoxazole (FCCS-17065-A)

The FCCS-17065-A-2-1 (400 mg, 1.277 mmol) obtained in Step 1 and potassium superoxide ($KO_2$) (454 mg, 6.386 mmol) were put into a container in an Ar gas atmosphere, acetonitrile (MeCN) (48 mL) was added thereto, and the resulting mixture was stirred at room temperature for 14 hours. After it was confirmed by thin layer chromatography (TLC) that all starting materials had disappeared, silica was added to and adsorbed to a crude product crude, and pressure was reduced. Silica-gel flash column chromatography (20% EtOAc/hexane, $R_f$=0.4) was performed to obtain 231 mg (white solid, 65%) of a target compound 2-[N-(3,4-dichlorophenyl)]aminobenzoxazole (FCCS-17065-A).

$^1$H NMR (400 MHz, $CD_3OD$); δ8.06 (d, 1H, J=2.8 Hz), 7.55 (dd, 1H, J=8.6, 2.6 Hz), 7.48-7.45 (m, 2H), 7.39 (d, 1H, J=8.0 Hz), 7.24 (td, 1H, J=7.6, 1.2 Hz), 7.16 (td, 1H, J=7.8, 1.2 Hz)

<Example 8> Preparation of N-(3,4-dichlorophenyl)naphtho[2,3-d]oxazol-2-amine (FCCS-17065-B)

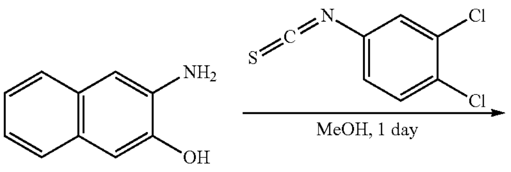

3-aminonaphthalen-2-ol

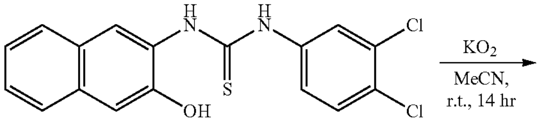

FCCS-17065-B-2-1

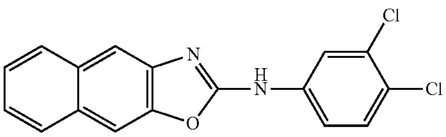

FCCS-17065-B

Step 1: Preparation of 1-(3,4-dichlorophenyl)-3-(3-hydroxynaphthalen-2-yl)thiourea (FCCS-17065-B-2-1)

After methanol (anhydrous MeOH) (7 mL) and chloroform ($CHCl_3$) (2 mL) were added to 3-amino-2-naphthol (350 mg, 2.119 mmol) in an Ar gas atmosphere and the resulting mixture was stirred at room temperature for 5 minutes, 3,4-dichlorophenyl isothiocyanate (0.38 mL, 2.638 mmol) was slowly added dropwise thereto and the resulting mixture was stirred at room temperature for 13 hours. After it was confirmed by thin layer chromatography (TLC) that all starting materials had disappeared and the solvent was removed by reducing pressure, dichloromethane (8 mL) was added thereto, the resulting mixture was stirred for 5 minutes, and then a solid which had not been dissolved was filtered to obtain 792 mg (white solid, 99%) of 1-(3,4-dichlorophenyl)-3-(3-hydroxynaphthalen-2-yl)thiourea (FCCS-17065-B-2-1).

$^1$H NMR (400 MHz, DMSO-$d_6$); δ10.48 (s, 1H), 10.34 (s, 1H), 9.57 (s, 1H), 8.59 (s, 1H), 8.05 (d, 1H, J=2.0 Hz), 7.73 (d, 1H, J=8.0 Hz), 7.67 (d, 1H, J=7.6 Hz), 7.60 (d, 1H, J=8.4 Hz), 7.52 (dd, 1H, J=8.6, 2.2 Hz), 7.35 (t, 1H, J=7.2 Hz), 7.27 (t, 1H, J=7.6 Hz), 7.24 (s, 1H)

Step 2: Preparation of N-(3,4-dichlorophenyl)naphtho[2,3-d]oxazol-2-amine (FCCS-17065-B)

The FCCS-17065-B-2-1 (400 mg, 1.101 mmol) obtained in Step 1 and potassium superoxide ($KO_2$) (391 mg, 5.505 mmol) were put into a container in an Ar gas atmosphere, acetonitrile (MeCN) (42 mL) was added thereto, and the resulting mixture was stirred at room temperature for 14 hours. After it was confirmed by thin layer chromatography (TLC) that all starting materials had disappeared, silica was added to and adsorbed to a crude product crude, and pressure was reduced. Silica-gel flash column chromatography (20% EtOAc/hexane, $R_f$=0.5) was performed to obtain 236 mg (white solid, 65%) of a target compound N-(3,4-dichlorophenyl)naphtho[2,3-d]oxazol-2-amine (FCCS-17065-B).

$^1$H NMR (400 MHz, DMSO-$d_6$); δ11.22 (s, 1H), 8.20 (d, 1H, J=2.0 Hz), 7.98-7.95 (m, 4H), 7.72 (dd, 1H, J=8.8, 2.4 Hz), 7.66 (d, 1H, J=8.4 Hz), 7.47-7.41 (m, 2H)

<Example 9> Preparation of N-(3,4-difluorophenyl)-5-methylbenzo[d]oxazol-2-amine (FCCS-17065-C)

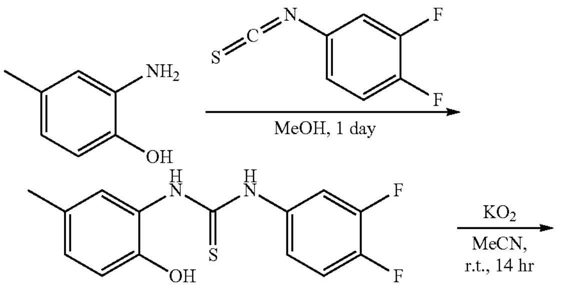

FCCS-17065-C-2-1

-continued

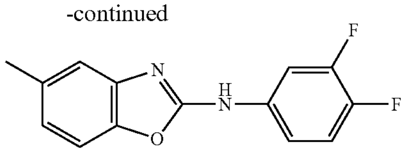

FCCS-17065-C

Step 1: Preparation of 1-(3,4-difluorophenyl)-3-(2-hydroxy-5-methylphenyl)thiourea (FCCS-17065-C-2-1)

After methanol (anhydrous MeOH) (8 mL) was added to and dissolved in 2-amino-p-cresol (300 mg, 2.436 mmol) in an Ar gas atmosphere, 3,4-difluorophenyl isothiocyanate (0.37 mL, 2.923 mmol) was slowly added dropwise thereto and the resulting mixture was stirred at room temperature for 13 hours. It was confirmed by thin layer chromatography (TLC) that all starting materials had disappeared, the solvent was removed by reducing pressure, and then silica was added to and adsorbed to a crude product, and silica-gel flash column chromatography (30% EtOAc/hexane, $R_f$=0.4) was performed to obtain 710 mg (white foamy solid, 99%) of 1-(3,4-difluorophenyl)-3-(2-hydroxy-5-methylphenyl)thiourea (FCCS-17065-C-2-1).

$^1$H NMR (400 MHz, $CD_3OD$); δ7.57-7.52 (m, 1H), 7.40 (s, 1H), 7.25-7.13 (m, 2H), 6.91 (dd, 1H, J=8.0, 1.6 Hz), 6.79 (d, 1H, J=8.0 Hz), 2.25 (s, 3H)

Step 2: Preparation of N-(3,4-difluorophenyl)-5-methylbenzo[d]oxazol-2-amine (FCCS-17065-C)

The FCCS-17065-C-2-1 (400 mg, 1.359 mmol) obtained in Step 1 and potassium superoxide ($KO_2$) (483 mg, 6.795 mmol) were put into a container in an Ar gas atmosphere, acetonitrile (MeCN) (52 mL) was added thereto, and the resulting mixture was stirred at room temperature for 14 hours. After it was confirmed by thin layer chromatography (TLC) that all starting materials had disappeared, silica was added to and adsorbed to a crude product crude, and pressure was reduced. Silica-gel flash column chromatography (20% EtOAc/hexane, $R_f$=0.45) was performed to obtain 224 mg (white solid, 63%) of a target compound N-(3,4-difluorophenyl)-5-methylbenzo[d]oxazol-2-amine (FCCS-17065-C).

$^1$H NMR (400 MHz, $CD_3OD$); δ=7.83-7.78 (m, 1H), 7.33-7.29 (m, 1H), 7.27-7.20 (m, 3H), 6.97-6.95 (m, 1H), 2.41 (s, 3H)

<Example 10> Synthesis of N-(3,4-difluorophenyl)benzo[d]oxazol-2-amine (FCCS-19025)

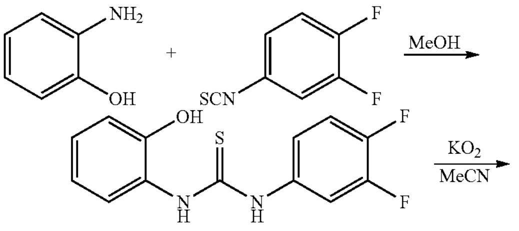

FCCS-19025-2-1

-continued

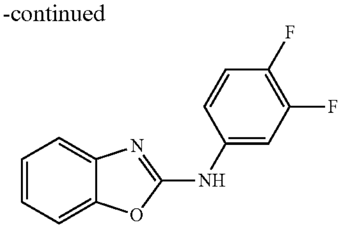

FCCS-19025

Step 1: Preparation of 1-(3,4-difluorophenyl)-3-(2-hydroxyphenyl)thiourea (FCCS-19025-2-1)

After 2-aminophenol (150 mg, 1.37 mmol) was dissolved in methanol (8 mL) in an Ar gas atmosphere, 3,4-difluorophenyl isothiocyanate (224 μl, 1.65 mmol) was slowly added thereto, and then the resulting mixture was stirred at room temperature for 13 hours. After the termination of the reaction was confirmed by thin layer chromatography (TLC), methanol was removed under reduced pressure. The reaction mixture was purified by silica-gel column chromatography (20% acetone/n-hexane) to obtain 1-(3,4-difluorophenyl)-3-(2-hydroxyphenyl)thiourea (FCCS-19025-2-1) as a light yellow solid (354 mg, 92%).

$^1$H-NMR (400 MHz, MeOH-$d_4$) δ7.62 (d, J=8.0 Hz, 1H), 7.55 (ddd, J=2.4 Hz, 1H), 7.25-7.13 (m, 2H), 7.11-7.05 (m, 1H), 6.92-6.82 (m, 2H); ESI-(+) 281.3 $[M+H]^+$.

Step 2: Preparation of N-(3,4-difluorophenyl)benzo[d]oxazol-2-amine (FCCS-19025)

The FCCS-19025-2-1 (224 mg, 0.80 mmol) obtained in Step 1 and potassium superoxide ($KO_2$) (284 mg, 4.00 mmol) were dissolved in acetonitrile (MeCN) (25 mL) in an Ar gas atmosphere, the resulting mixture was stirred at room temperature for 14 hours. After the termination of the reaction was confirmed by thin layer chromatography (TLC), acetonitrile (MeCN) was removed under reduced pressure. The reaction mixture was purified by silica-gel column chromatography (10 to 20% ethyl acetate/n-hexane) to obtain a target compound N-(3,4-difluorophenyl)benzo[d]oxazol-2-amine (FCCS-19025) as a white solid (160 mg, 82%).

$^1$H-NMR (400 MHz, MeOH-$d_4$) δ7.82 (ddd, J=2.8 Hz, 1H), 7.42 (d, J=7.6 Hz, 1H), 7.36 (d, J=8.0 Hz, 1H), 7.34-7.29 (m, 1H), 7.28-7.18 (m, 2H), 7.16-7.10 (m, 1H); ESI-(+) 247.2 $[M+H]^+$.

The chemical structural formulae of Examples 1 to 10 are shown in the following Table 1.

TABLE 1

| Example | Chemical structural formula |
|---|---|
| Example 1 (FCCS-17064) | 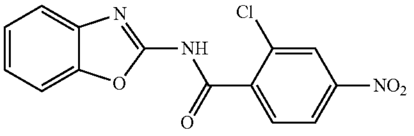 [SMILES: O=C(Nc1nc2ccccc2o1)c1ccc([N+](=O)[O-])cc1Cl] |
| Example 2 (FCCS-17065) | 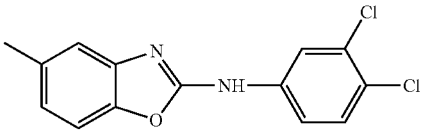 [SMILES: Cc1ccc2oc(Nc3ccc(Cl)c(Cl)c3)nc2c1] |
| Example 3 (FCCS-17066) | 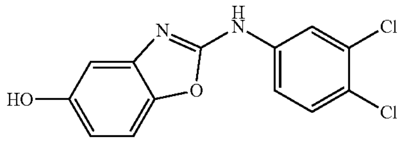 [SMILES: Oc1ccc2oc(Nc3ccc(Cl)c(Cl)c3)nc2c1] |
| Example 4 (FCCS-17067) | 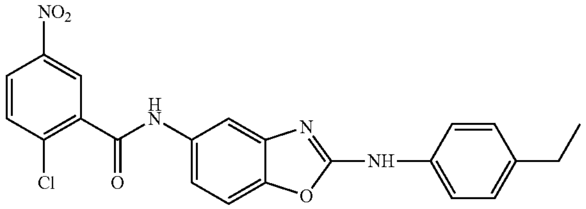 [SMILES: CCc1ccc(Nc2nc3cc(NC(=O)c4cc([N+](=O)[O-])ccc4Cl)ccc3o2)cc1] |
| Example 5 (FCCS-17068) | 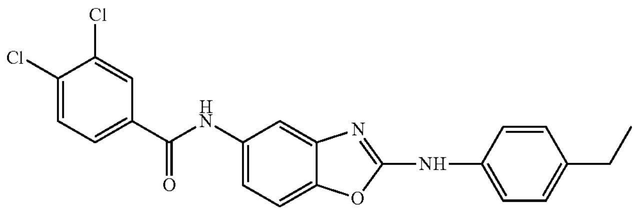 [SMILES: CCc1ccc(Nc2nc3cc(NC(=O)c4ccc(Cl)c(Cl)c4)ccc3o2)cc1] |

TABLE 1-continued

| Example | Chemical structural formula |
|---|---|
| Example 6 (FCCS-17069) | 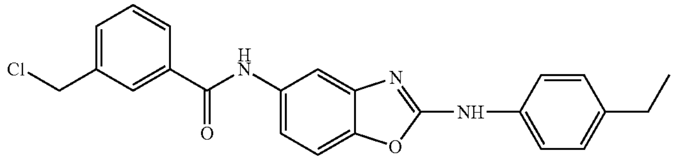 [SMILES: CCc1ccc(Nc2nc3cc(NC(=O)c4cccc(CCl)c4)ccc3o2)cc1] |
| Example 7 (FCCS-17065-A) | 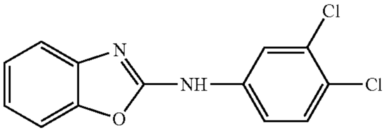 [SMILES: Clc1ccc(Nc2nc3ccccc3o2)cc1Cl] |
| Example 8 (FCCS-17065-8) | 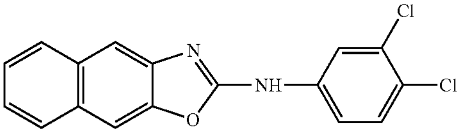 [SMILES: Clc1ccc(Nc2nc3cc4ccccc4cc3o2)cc1Cl] |
| Example 9 (FCCS-17065-C) | 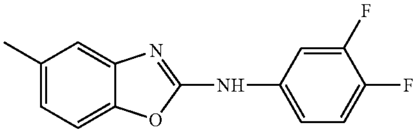 [SMILES: Cc1ccc2oc(Nc3ccc(F)c(F)c3)nc2c1] |
| Example 10 (FCCS-19025) | 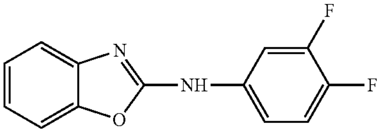 [SMILES: Fc1ccc(Nc2nc3ccccc3o2)cc1F] |

Comparative Example 1

N-(2-chlorophenyl)-1H-indole-3-carboxamide was used as Comparative Example 1.

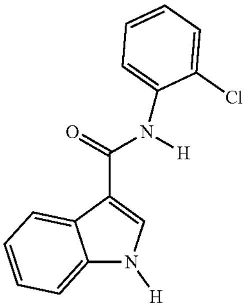 [SMILES: O=C(Nc1ccccc1Cl)c1c[nH]c2ccccc12]

Comparative Example 2

2'-Chloroacetanilide (C0621) was purchased and used as Comparative Example 2.

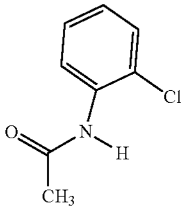

Comparative Example 3

N-methyl-1H-indole-3-carboxamide (FCCS-16030) was purchased and used as Comparative Example 3.

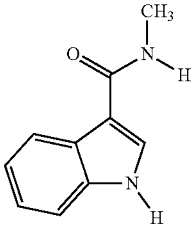

<Comparative Example 4> Preparation of N-(2-((2-chlorophenyl)amino)-2-oxoethyl)-1H-indole-3-carboxamide (FCCS-16031)

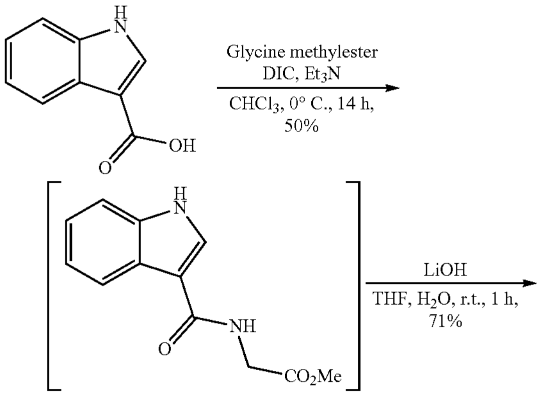

FCCS-16031-3-1

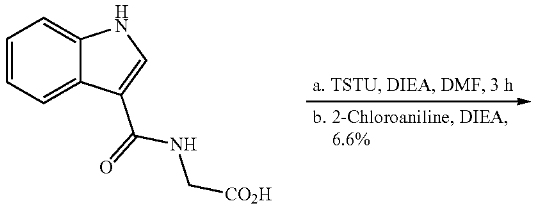

FCCS-16031-3-2

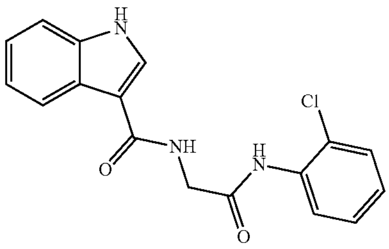

FCCS-16031

Step 1: Preparation of methyl 2-(1H-indole-3-carboxamido)acetate (CCS-16031-3-1)

Indole-3-carboxylic acid (600 mg, 3.72 mmol) and glycine methyl ester (467 mg, 3.72 mmol) were dissolved in chloroform (11 mL), and the resulting solution was cooled in an ice bath. After triethylamine (1.04 mL, 7.446 mmol) and N,N-diisopropylcarbodiimide were additionally added thereto, the resulting mixture was stirred at 0° C. for 14 hours. The mixture was washed with a 10% aqueous $NaHCO_3$ solution, and then washed with a 5% HCl aqueous solution, and the remaining moisture was removed by allowing the resulting mixture to pass through an anhydrous $Na_2SO_4$ pad, and then the solvent was removed under reduced pressure. 430 mg (white solid, 50%) of methyl 2-(1H-indole-3-carboxamido)acetate (CCS-16031-3-1) was obtained in a mixture state by performing silica-gel flash column chromatography (70% ethyl acetate/n-hexane). The next step was performed without further purification. ESI-MS: 231.2 $[M-H]^-$

Step 2: Preparation of 2-(1H-indole-3-carboxamido) acetic acid (FCCS-16031-3-2)

The methyl 2-(1H-indole-3-carboxamido)acetate (CCS-16031-3-1) (220 mg, 0.947 mmol) was dissolved in tetrahydrofuran (6 mL), a solution of a lithium hydroxide hydrate (LiOH monohydrate) (131 mg, 3.126 mmol) dissolved in water (2 mL) was added thereto, and the resulting mixture was stirred for 1 hour. After the pH was adjusted to 2 by adding a 1.0 N aqueous HCl solution, the mixture was extracted with ethyl acetate. After the remaining moisture was removed by allowing the mixture to pass through an anhydrous $Na_2SO_4$ pad, the solvent was removed under reduced pressure. 147 mg (yellow foamy solid, 71%) of 2-(1H-indole-3-carboxamido)acetic acid (FCCS-16031-3-2) was obtained by performing silica-gel flash column chromatography (10% methanol/dichloromethane).

$^1H$ NMR (400 MHz, $CD_3OD$); δ8.10-8.08 (m, 1H), 7.92 (s, 1H), 7.43 (dt, J=8.0, 1.2 Hz, 1H), 7.17 (quint d, J=7.2, 1.6 Hz, 2H), 4.12 (s, 2H)

Step 3: Preparation of N-(2-((2-chlorophenyl) amino)-2-oxoethyl)-1H-indole-3-carboxamide (FCCS-16031)

The 2-(1H-indole-3-carboxamido)acetic acid (FCCS-16031-3-2) (200 mg, 0.917 mmol) and N,N,N',N'-tetramethyl-O—(N-succinimidyl)uronium tetrafluoroborate (TSTU) (290 mg, 0.962 mmol) were dissolved in N,N-dimethylformamide (4 mL, anhydrous) in an Ar gas atmosphere, N,N-diisopropylethylamine (DIEA) (0.4 mL, 2.293 mmol) was added thereto, and then the resulting mixture was stirred at room temperature for 3 hours. 2-Chloroaniline (0.29 mL, 2.751 mmol) and N,N-diisopropylethylamine (DIEA) (0.64 mL, 3.668 mmol) were added thereto, and the resulting mixture was heated at 60° C. for 4 hours. After the solvent was removed under reduced pressure, an organic layer was obtained by adding dichloromethane and a saturated aqueous $NH_4Cl$ solution thereto for extraction, the remaining moisture was removed by allowing the organic layer to pass through an anhydrous $Na_2SO_4$ pad, and then the solvent was removed under reduced pressure. 20 mg (white solid, 6.6%) of a target compound N-(2-((2-chlorophenyl) amino)-2-oxoethyl)-1H-indole-3-carboxamide (FCCS-16031) was obtained by performing silica-gel flash column chromatography (70% ethyl acetate/n-hexane).

$^1H$ NMR (400 MHz, $CD_3OD$); δ8.15-8.12 (m, 1H), 8.04 (dd, J=8.0, 1.2 Hz, 1H), 7.97 (s, 1H), 7.46-7.41 (m, 2H), 7.33-7.28 (m, 1H), 7.23-7.12 (m, 3H), 4.26 (s, 2H)

<Experimental Example 1-1> Luciferase Expression Experiment (Comparative Examples 1 to 4)

In order to evaluate whether the klotho gene was expressed by the evaluation of luciferase activity, human renal proximal tubule epithelial cells (RPTECs) (ATCC CRL-4031), which are epithelial cells of the proximal tubule of the human kidneys, were purchased from Lonza, USA and used.

For culturing, a Renal Epithelial Growth Medium (REGM™) Bullet kit, also manufactured by the same Lonza company, was used, and the cells were cultured under conditions of 37° C. and 5% $CO_2$. As a plasmid for luciferase expression, a plasmid in which the promoter site of a human KL (klotho) gene was disposed to regulate the expression of a firefly luciferase gene was used.

The plasmid was incorporated into cells using an X-treme GENE transfection reagent from Roche. The activity of luciferase expressed in cells was measured using a Dual-Luciferase reporter assay system manufactured by Promega. After the cultured cells were treated with each compound at an indicated concentration for 24 hours, the activity of luciferase was measured. It is indirectly shown that the expression of the klotho gene may be increased when the activity of luciferase is high.

The expression of a reporter gene was confirmed by treating RPTEC cells with Comparative Examples 1 to 4 at a concentration of 5 μM and using a reporter gene including a promoter from the start site of the human klotho gene to a front of 1.7 kbp or a reporter gene including a promoter from the start site of the human klotho gene to a front of 240 bp.

Figure 1B:
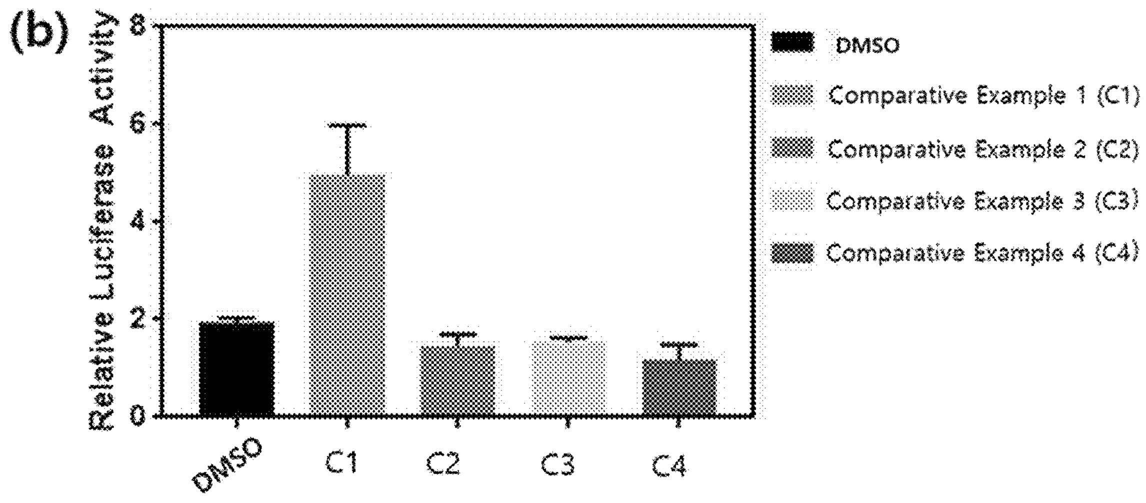
FIG. 1B illustrates the results of luciferase expression experiments using a reporter gene including a promoter from the start site of the human klotho gene of Comparative Examples 1 to 4 to the front of 240 bp.

As a result, as illustrated in FIG. 1, it was confirmed that the luciferase activity of the compound of Comparative Example 1 was the highest.

<Experimental Example 1-2> Luciferase Expression Experiment (Examples 1 to 6)

Based on the results of Experimental Example 1-1, Examples 1 to 6 having a chemical structure similar to that of Comparative Example 1 were synthesized, and the present Experimental Example 1-2 was performed.

Figure 2:
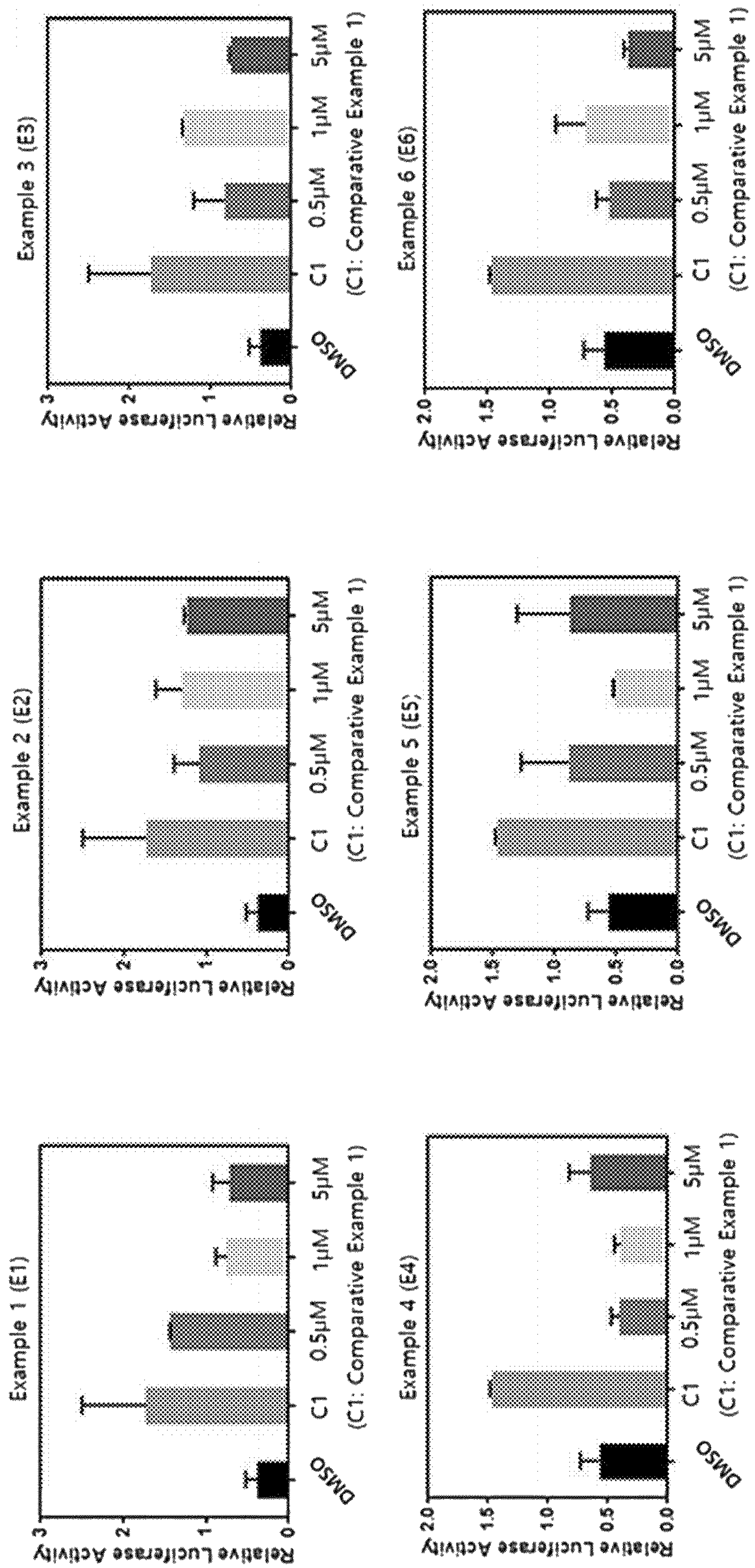
FIG. 2 illustrates the results of luciferase expression experiments using a reporter gene including a promoter included up to −2.1 kb upstream of the human klotho gene of Examples 1 to 6.
Figure 3:
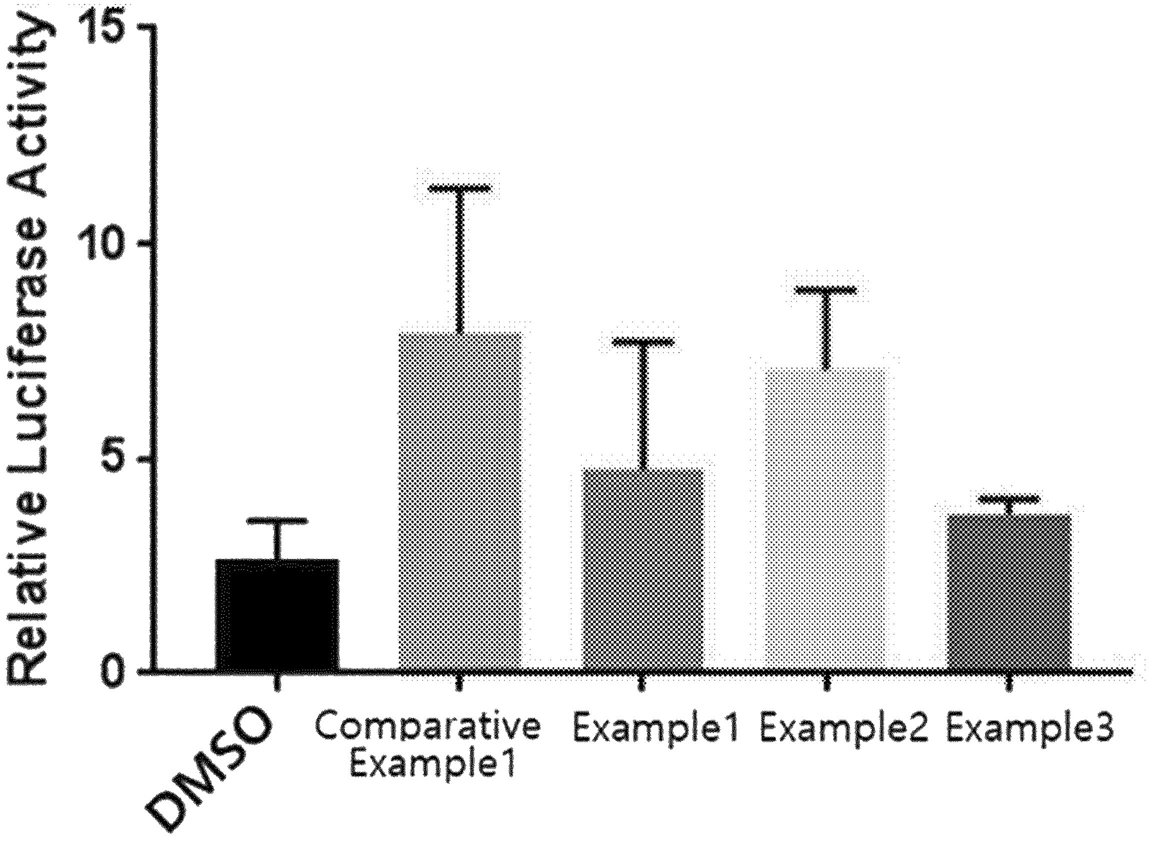
FIG. 3 illustrates the results of luciferase expression experiments using a reporter gene including a promoter included up to −2.1 kb upstream of the human klotho gene of Examples 1 to 3.

The results of confirming the expression of a reporter gene by treating RPTECs, which are epithelial cells of the proximal tubule of the human kidneys, with Examples 1 to 6 at concentrations of 0.5, 1 and 5 μM and Comparative Example 1 at a concentration of 5 μM and using a reporter gene (pHKP-luc) including a promoter included up to −2.1 kb upstream of the human klotho gene are illustrated in FIGS. 2 and 3.

As illustrated in FIG. 2, it was confirmed that the expression of the reporter genes of the compounds of Examples 1 and 2 was at a level similar to that of Comparative Example 1.

As illustrated in FIG. 3, as a result of confirming the expression of a reporter gene by treating RPTEC cells with Comparative Example 1 and Examples 1 to 3 at a concentration of 5 μM and using the reporter gene (pHKP-luc) including a promoter included up to −2.1 kb upstream of the human klotho gene, it was confirmed that the compound of Example 2 was at a level similar to that of Comparative Example 1.

<Experimental Example 2> Quantitative Evaluation of Klotho (KL) Gene Expression Level Using Real-Time PCR Experiment For RNA extraction from RPTEC cells, which are epithelial cells of the proximal tubule of the human kidneys, treated with the compounds of Comparative Example 1 and Examples 1 and 2 for 6 hours, an RNeasy kit from Qiagen Inc. was used. The results of preparing cDNA from extracted RNA using a Superscript II kit from Thermo Fisher Scientific, Inc. and performing the quantitative evaluation using Taqman Gene Expression assays from Applied Biosystems as a klotho (KL) gene-specific kit are illustrated in FIG. 4.

Figure 4:
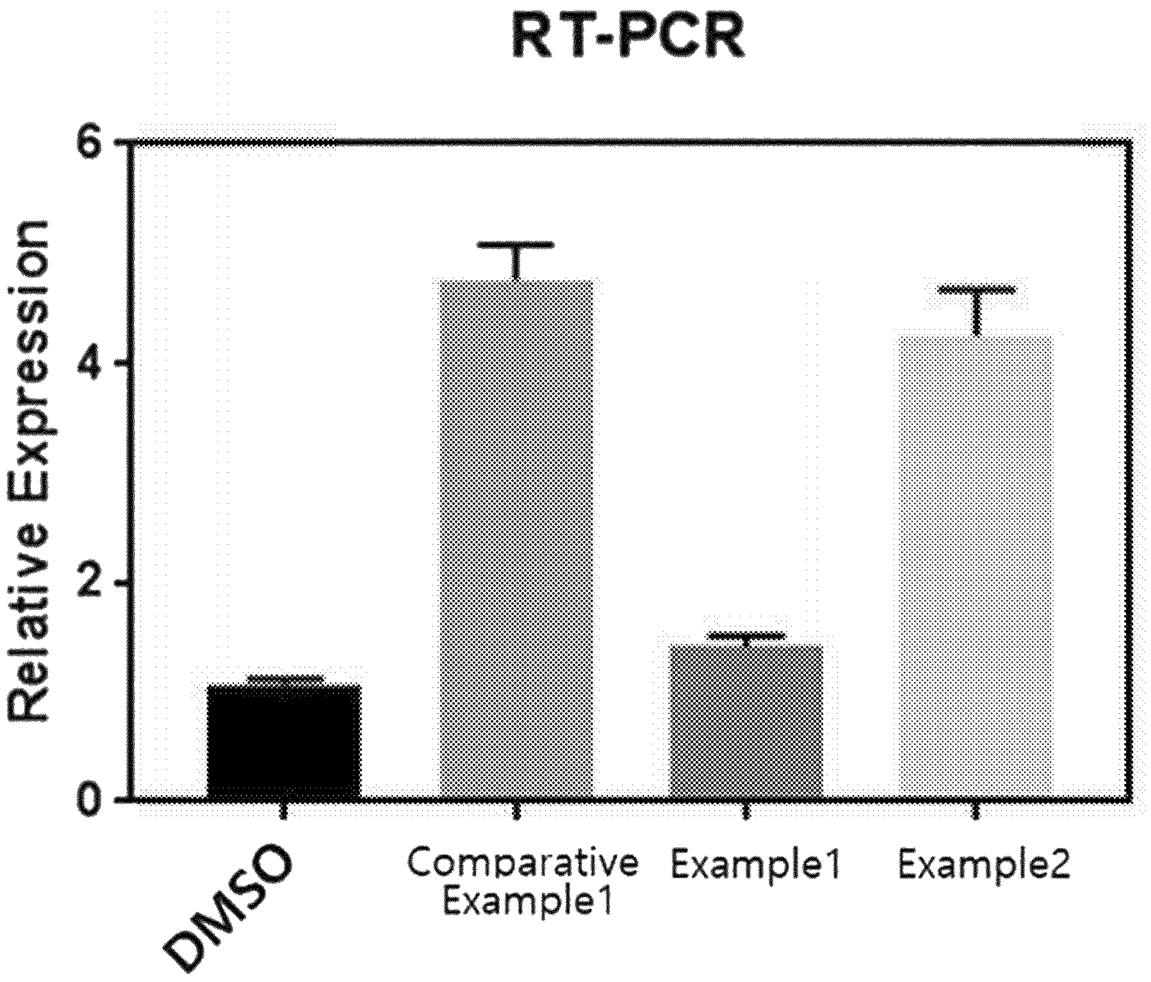
FIG. 4 is a result of confirming the mRNA expression level of the klotho (KL) gene in Examples 1 and 2 by RT-PCR.

As illustrated in FIG. 4, it was confirmed that the compound of Example 2 was at a level similar to that of Comparative Example 1.

Based on the results of the present Experimental Example 2, the compounds of Examples 7 to 10 having a chemical structure similar to the compound of Example 2 were synthesized and used in the following Experimental Example 3.

<Experimental Example 3> Quantitative Evaluation of Klotho (KL) Gene Expression Level Using General PCR Experiment After RPTEC cells, which are epithelial cells of the proximal tubule of the human kidneys, were each treated with the compounds of Examples 7 to 10 at 2.5 μM for 6 hours, RNA was extracted from the cells, and cDNA was prepared from the extracted RNA using a Superscript II kit from Thermo Fisher Scientific, Inc., and then general PCR was performed.

Information on the primers used in the experiment is as follows.

KL-F GATAGAGAAAAATGGCTTCCCTCC (SEQ ID NO: 1)

KL-R GGTCGGTAAACTGAGACAGAGTGG (SEQ ID NO: 2)

GAPDH-F TGACAACTTTGGTATCGTGGAAGG (SEQ ID NO: 3)

GAPDH-R AGGGATGATGTTCTGGAGAGCC (SEQ ID NO: 4)

Figure 5:
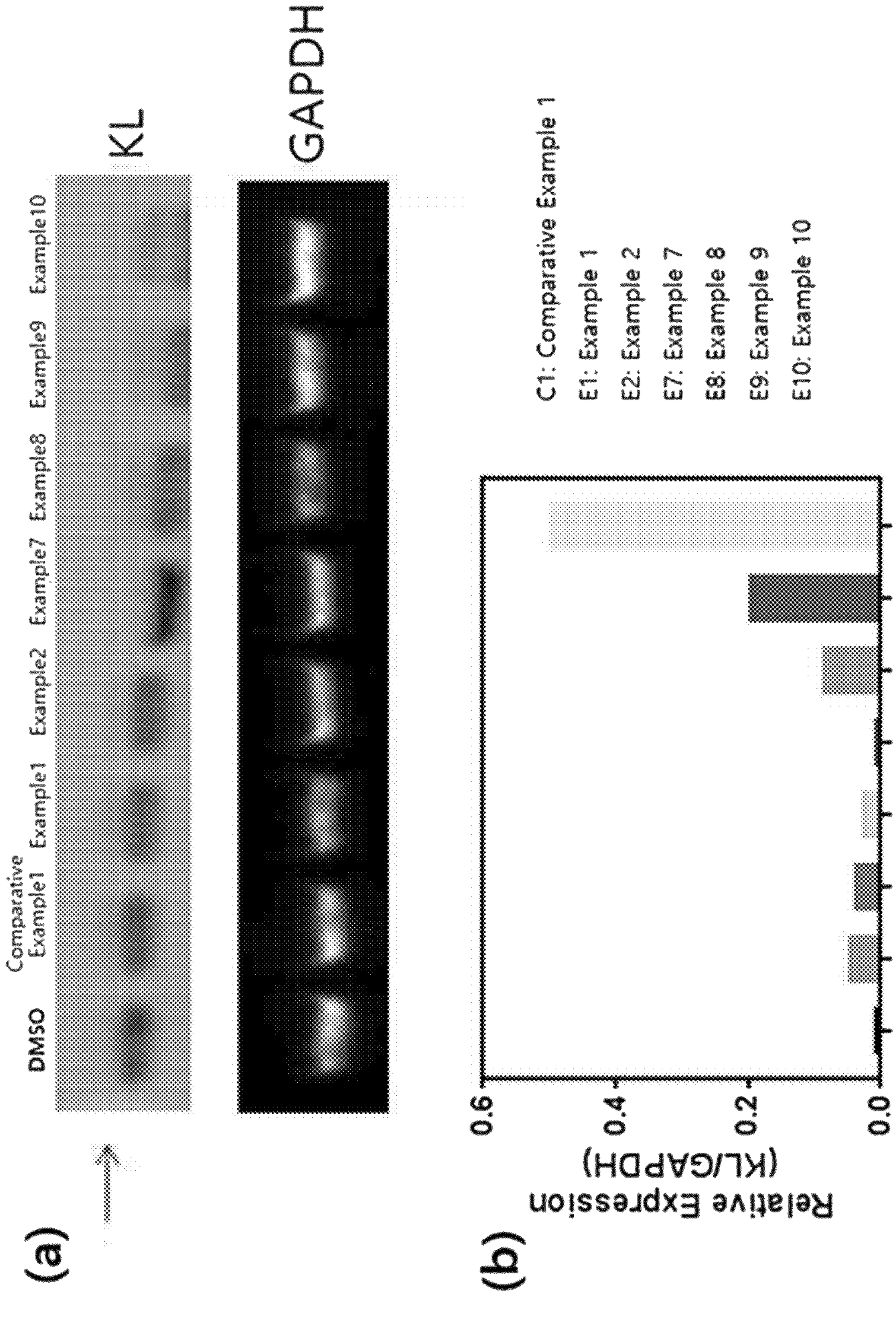
FIG. 5 is a result of confirming the expression of the klotho gene in RPTEC cells treated with the compounds of Examples 1 and 2 and Examples 7 to 10.

The DNA amplified by PCR was confirmed by staining with ethidium bromide after electrophoresis on an agarose gel, and the amounts of DNA in the band were quantitatively compared using the SPEedyQuant program, and are illustrated in FIG. 5.

As illustrated in FIG. 5, it was confirmed that the expression level of the klotho (KL) gene in Examples 8 to 10 was much higher than that in Comparative Example 1, and in particular, Example 10 showed an improvement to about 10 times the level of Comparative Example 1.

<Experimental Example 4> Toxicity Test

Cultured human kidney-2 (HK2) cells were treated with Comparative Example 1, Example 2 and Examples 9 to 10 at a concentration of 25 μM or 12.5 μM, and after 24 hours, cytotoxicity was measured using an EZ-Cytox kit. Since EZ-Cytox produces formazan having an absorbance at 450 nm by mitochondrial enzymes in living cells, living cells exhibit even higher absorbance at 450 nm. When the toxicity of cells treated with DMSO in the same volume as the amount of treated compound was set to 1, it was confirmed how much the cells were toxically reduced by the compound sample treatment, and the results are illustrated in FIG. 6.

Figure 6:
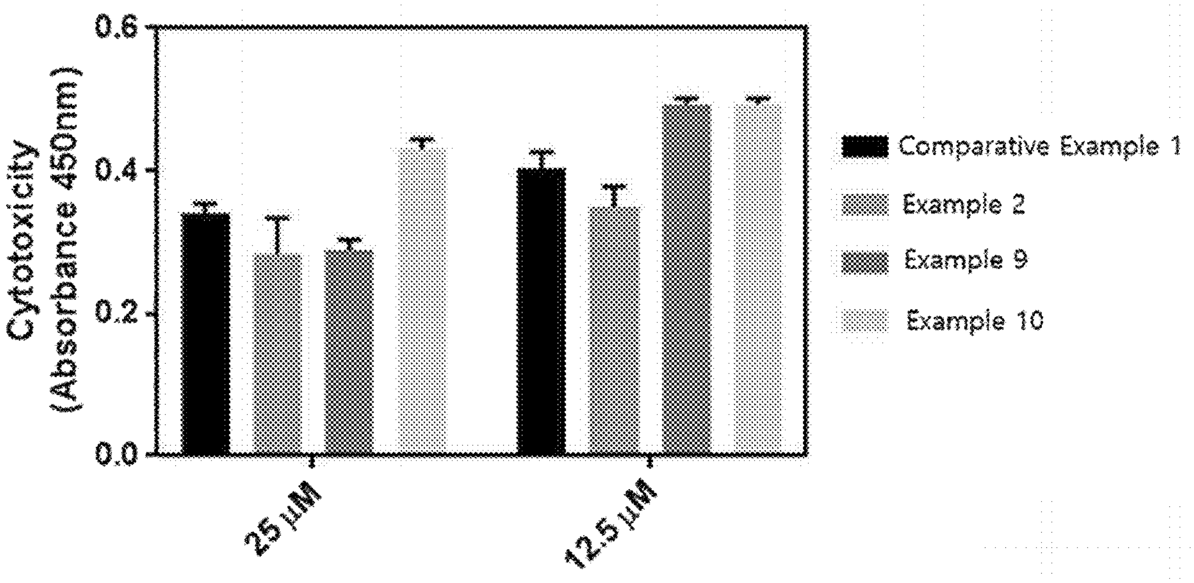
FIG. 6 is a result of confirming cytotoxicity in HK2 cells treated with the compounds of Examples 1, 9 and 10.

As illustrated in FIG. 6, it was confirmed that when the cells were treated at a concentration of 12.5 μM or 25 μM, the compound of Example 10 showed the least toxicity, and the toxicity showed an improvement of 20% or more even when compared to Comparative Example 1.

Figure 7A:
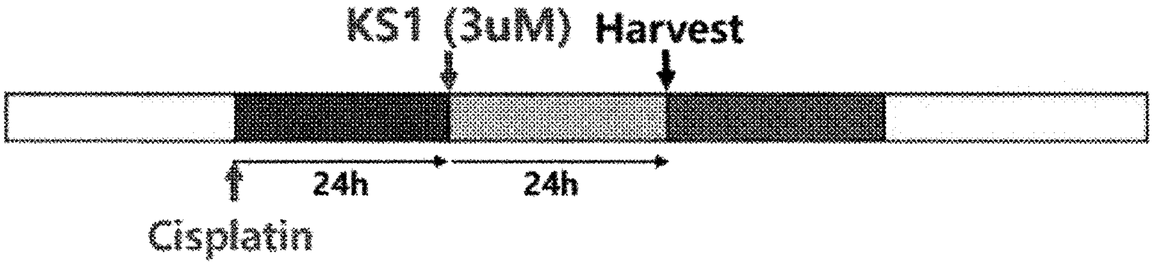
FIG. 7A schematically illustrates a protocol for creating a disease model by treating HK-2 cells (human kidney cells) with cisplatin.
Figure 7B:
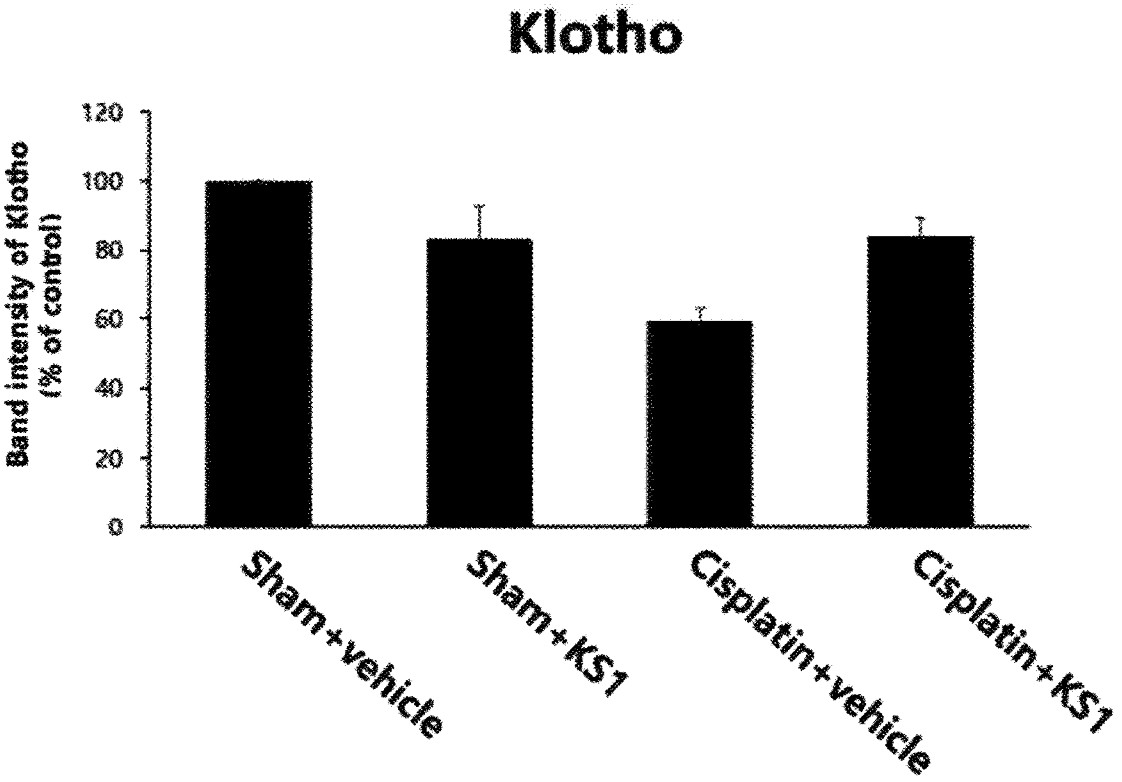
FIG. 7B is a result of analyzing the degree of the expression level of a klotho protein in HK-2 cells obtained according to the protocol of FIG. 7A.

<Experimental Example 5> Analysis of Klotho Protein Expression Level in HK-2 Cells As in the protocol in FIG. 7A, a disease model was made by treating HK-2 cells (human renal cells) with cisplatin (20 μM), and then treated with a KS1 compound (Example 10) (3 μM). After 24 hours, the expression degree of the klotho protein was confirmed by obtaining the cells. As illustrated in FIG. 7B, it was confirmed that the expression of the klotho protein in HK-2 cells was decreased in a group treated with cisplatin, and was increased in a group treated with the KS1 compound (Example 10).

Figure 8A:
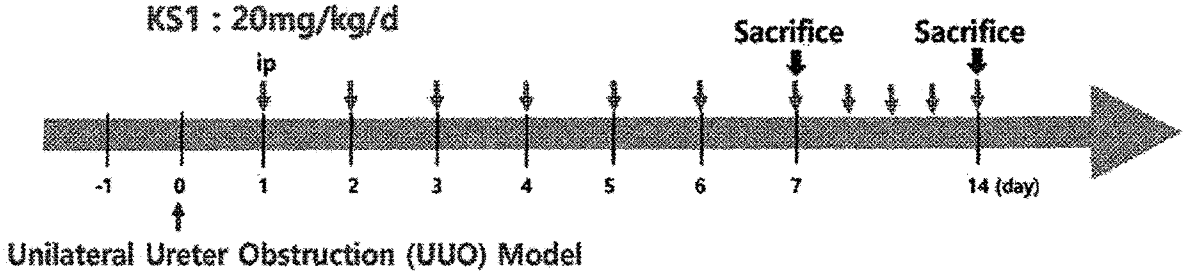
FIG. 8A schematically illustrates a protocol for obtaining an experimental sample by injecting a KS1 compound into a unilateral ureter obstruction animal model.

<Experimental Example 6> Analysis of Effect of KS1 Compound (Example 10) in Unilateral Ureter Obstruction (UUO) Model In a unilateral ureter obstruction model, 5-week-old male C56BL/6 mice were used. After the right ureter was tied with a thread to create a unilateral ureter obstruction model, the KS1 compound (20 mg/kg/day) was injected into the abdominal cavity daily starting 24 hours later. After that, samples were collected by sacrificing the mice on days 7 and 14 and tested (FIG. 8A).

Confirmation of Presence or Absence of Renal Hypertrophy

Figure 8B:
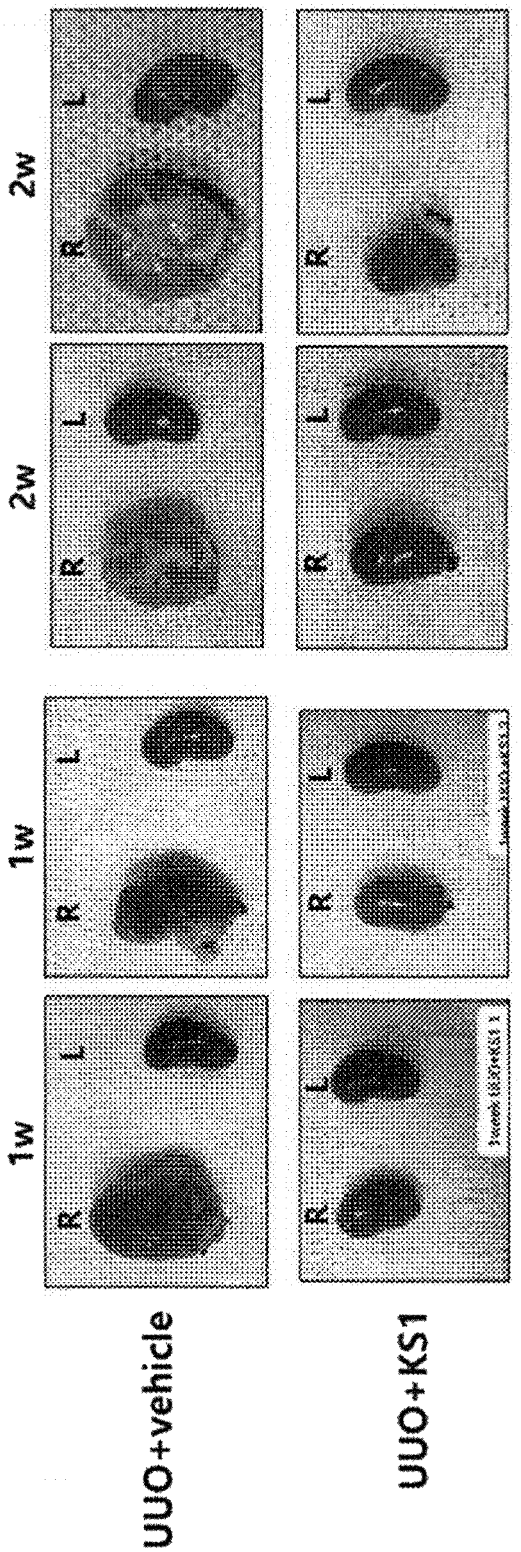
FIG. 8B is a result of analyzing the degree of renal hypertrophy using an experimental sample obtained according to the protocol of FIG. 8A.

As a result of the experiment, the unilateral ureter obstruction model showed a result that the kidneys were hypertrophied, and the kidneys treated with the KS1 compound showed a result that there was no difference in size (FIG. 8B).

Confirmation of Nuclear and Cytoplasmic Changes

Figure 9:
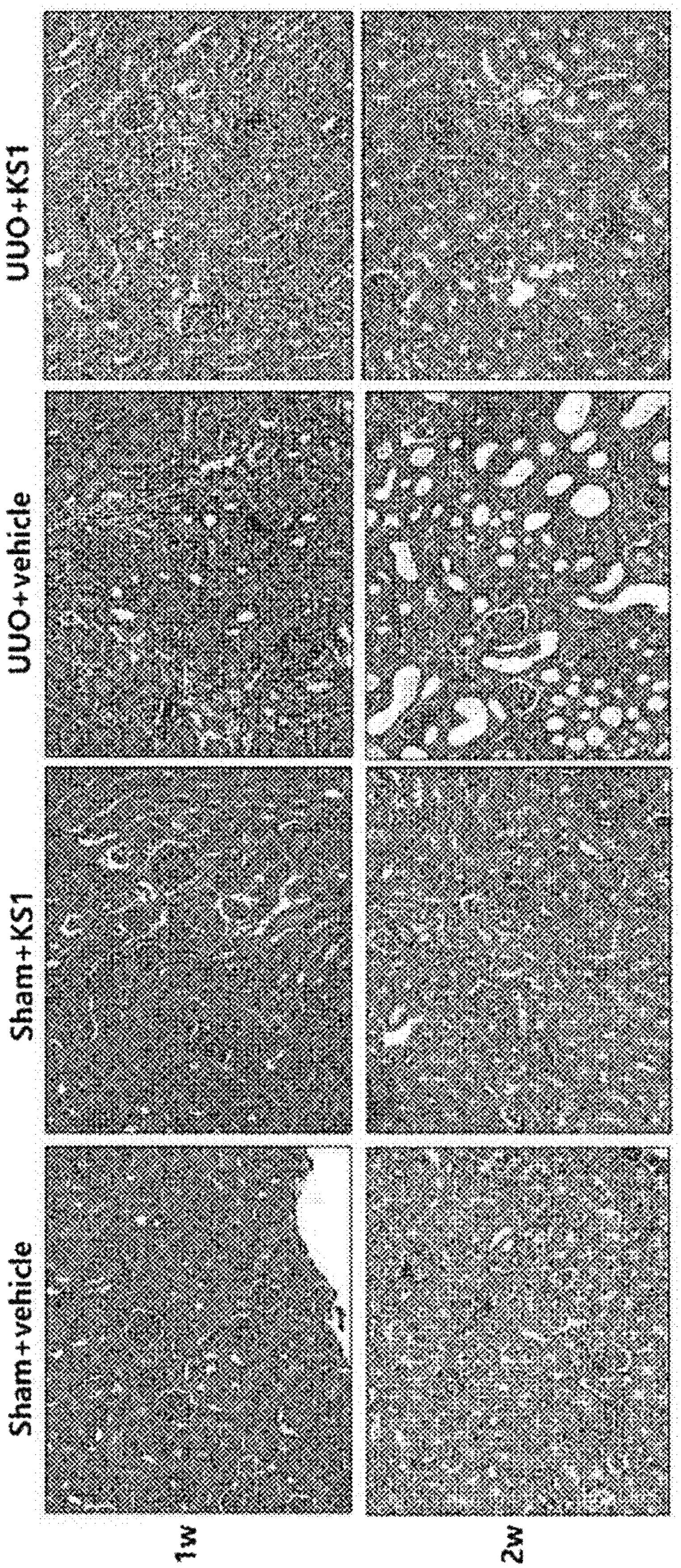
FIG. 9 is a result of confirming the changes in the nucleus and cytoplasm in a unilateral ureter obstruction model through H&E staining.

H&E staining was performed to investigate changes in the nucleus and cytoplasm in the unilateral ureter obstruction model, and the results are illustrated in FIG. 9. It could be seen that in the one-week sample of the unilateral ureter obstruction model which was not treated with KS1, the number of nuclei increased significantly, and the two-week sample showed that the cytoplasm was destroyed whereas the KS1-treated sample showed a large reduction in tissue destruction (FIG. 9).

Confirmation of Whether Fibrosis Progressed

Figure 10:
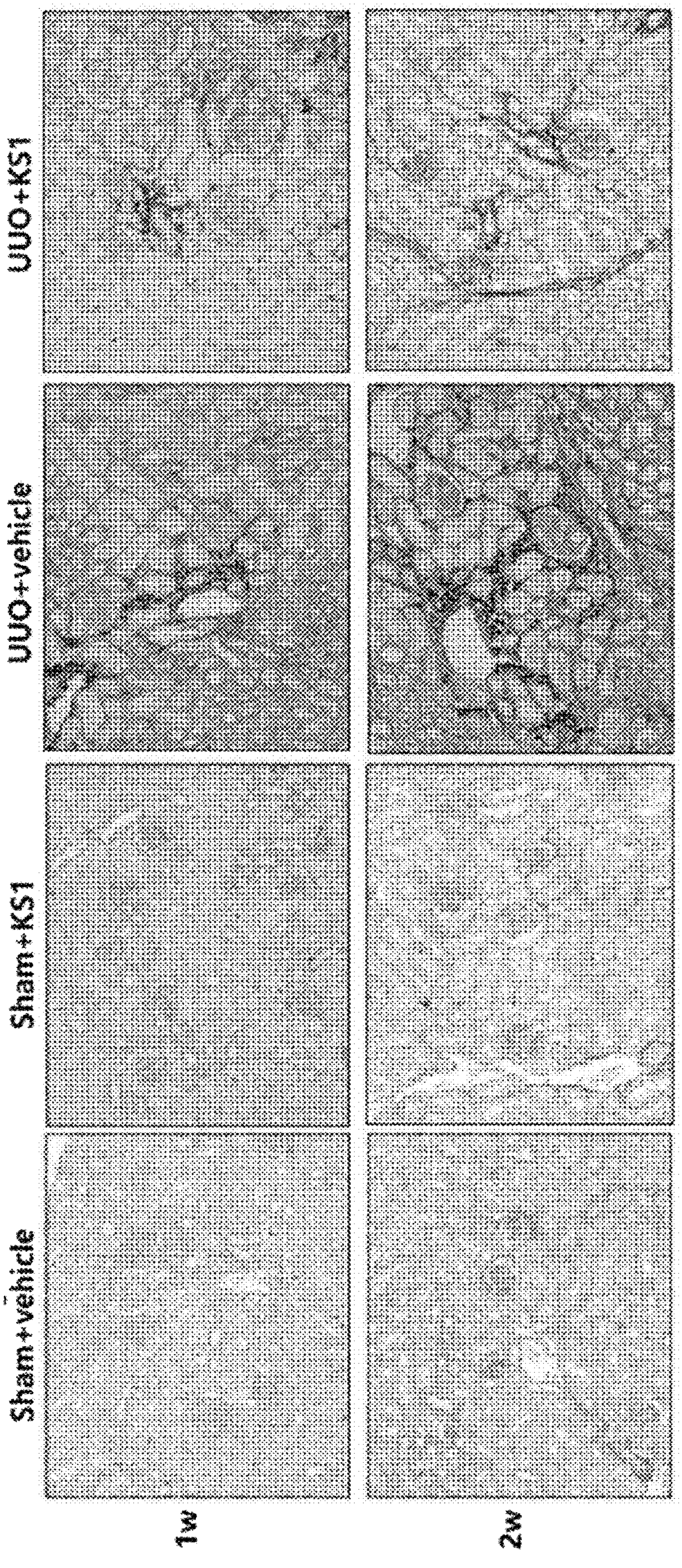
FIG. 10 is a result of confirming the degree of fibrosis progression in a unilateral ureter obstruction model through Sirius Red staining.

In addition, Sirius Red staining was performed to investigate the change according to the progress of fibrosis in the unilateral ureter obstruction model. In the one-week tissue sample of the unilateral ureter obstruction model that was not treated with KS1, it can be seen from the color red that fibrosis began to progress, and the two-week sample showed a result that fibrosis had progressed more than the one-week sample. However, the KS1 treatment group showed a result that fibrosis occurred less than the unilateral ureter obstruction model which was not treated with KS1 (FIG. 10).

Confirmation of Presence or Absence of Apoptosis

Figure 11A:
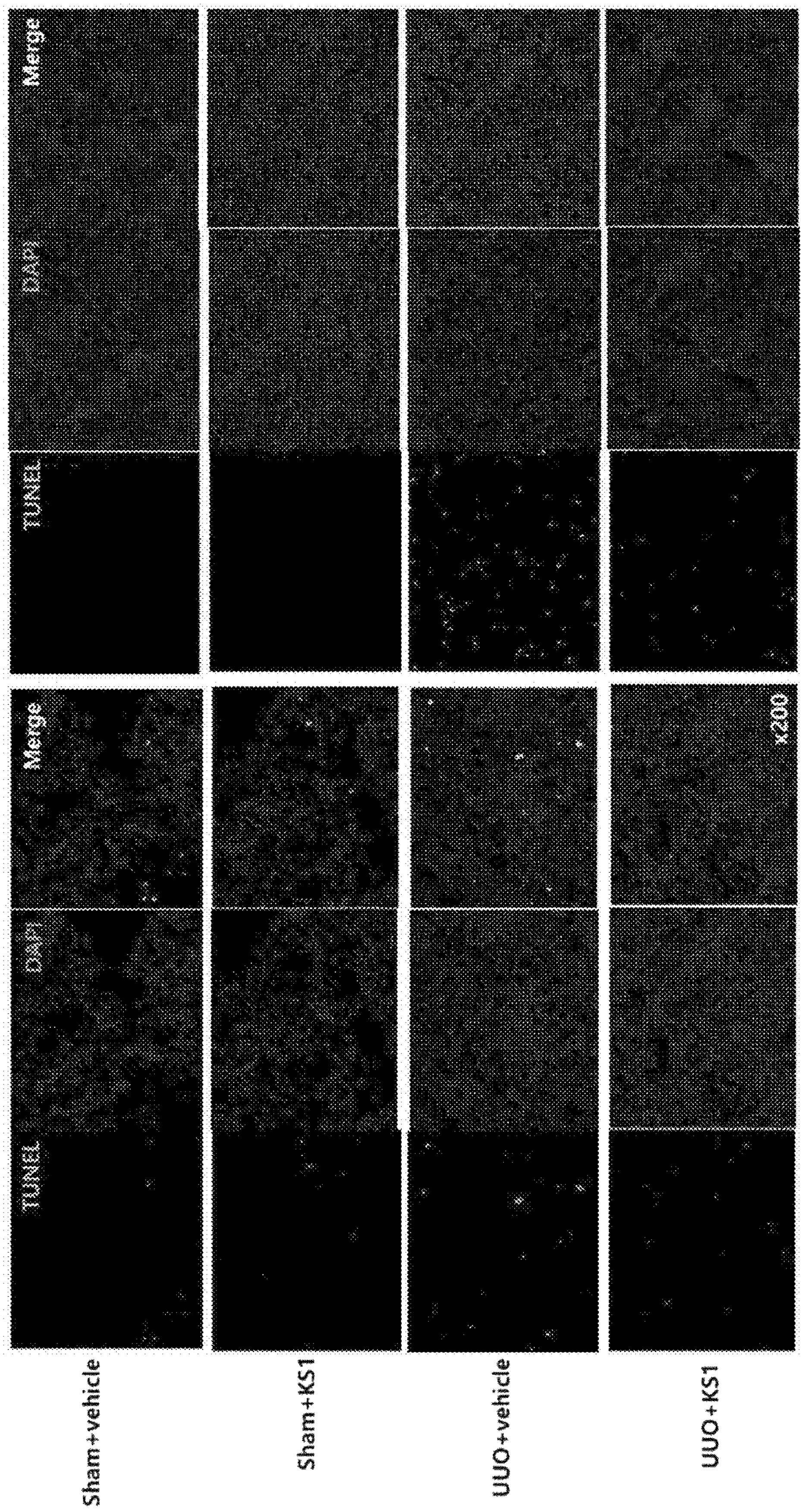
FIG. 11 is a result of confirming the degree of apoptosis in a unilateral ureter obstruction model through TUNEL staining.
Figure 11B:
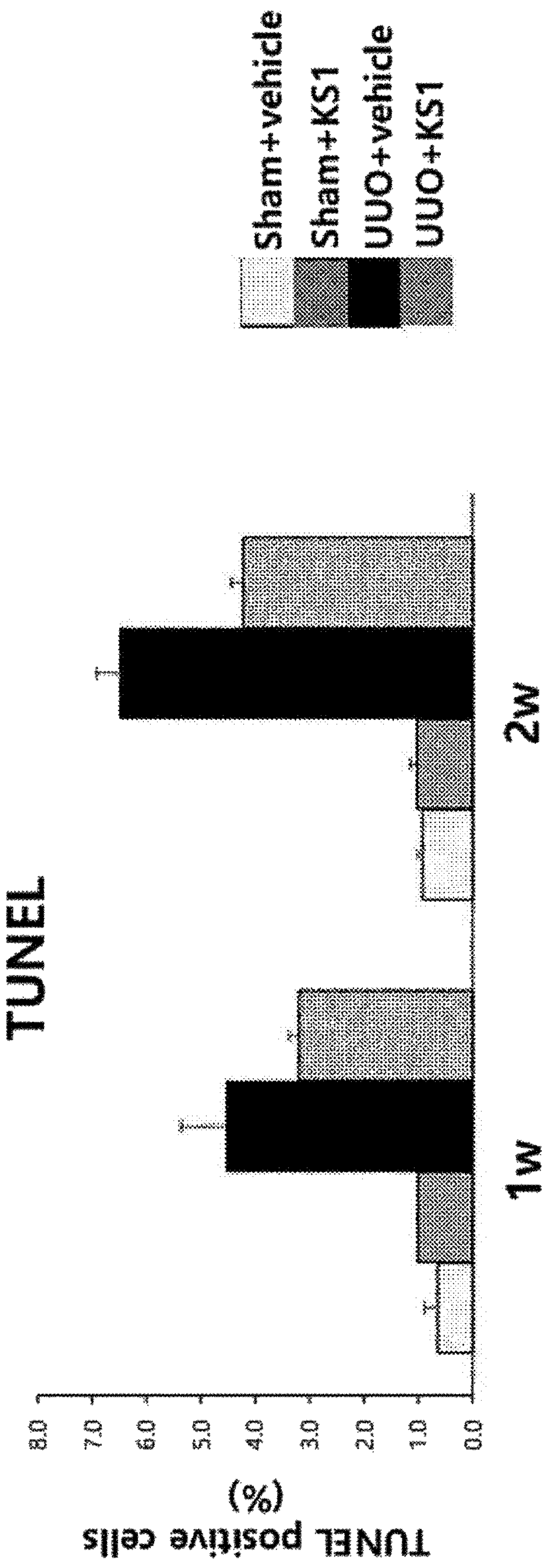

TUNEL staining was performed to investigate the degree of apoptosis in the unilateral ureter obstruction model. Apoptosis occurred in the one-week sample of the tissue of the unilateral ureter obstruction model which was not treated with KS1, and the two-week sample showed a result that apoptosis was increased compared to the one-week sample. However, the KS1 treatment group showed a result that apoptosis was remarkably reduced compared to the unilateral ureter obstruction model which was not treated with KS1 (FIG. 11).

Confirmation of Klotho Protein Expression Level

Figure 12:
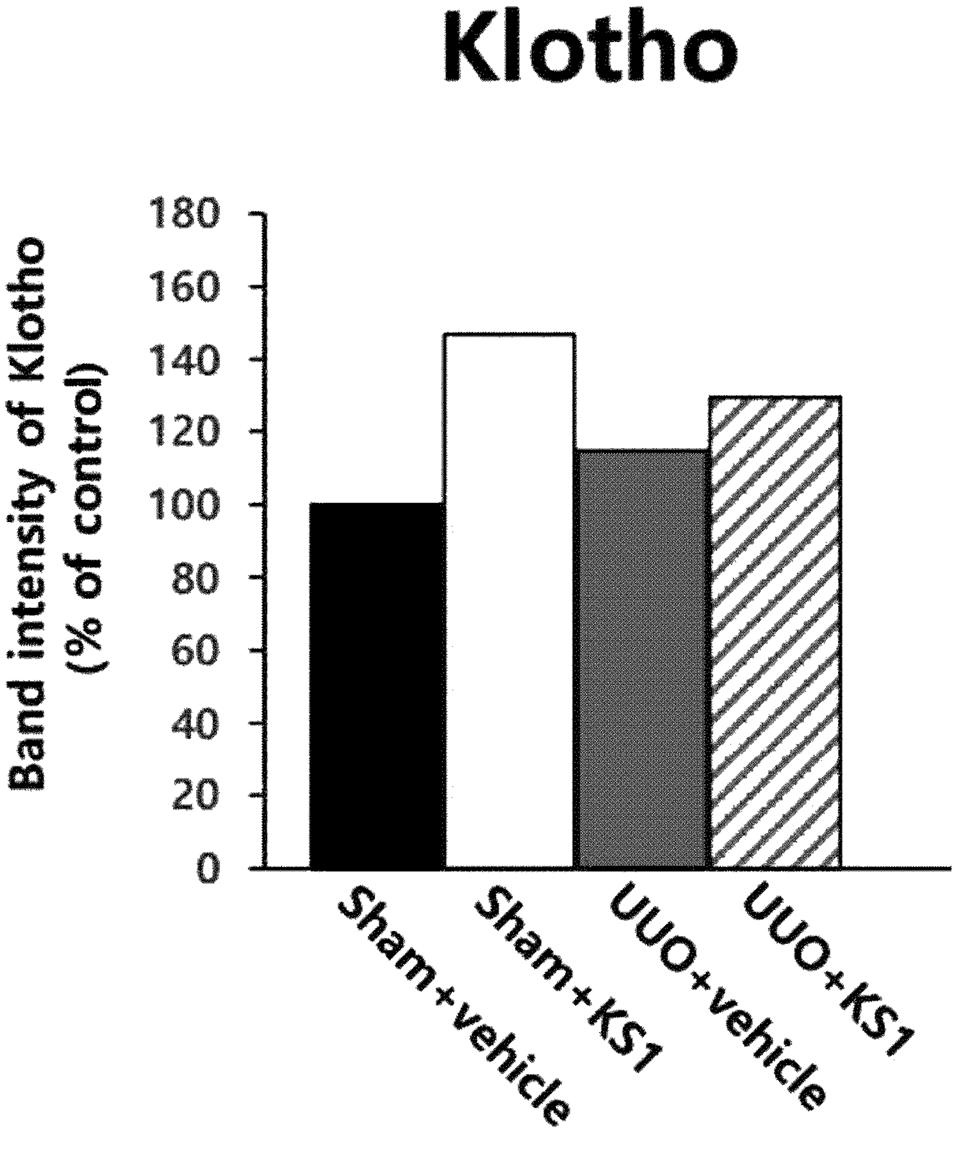
FIG. 12 is a result of analyzing changes in klotho protein expression in a unilateral ureter obstruction model.

As a result of confirming the change in klotho protein expression in the one-week sample of the unilateral ureter obstruction model, klotho protein was decreased in the unilateral ureter obstruction model sample which was not treated with KS1, but the case of treatment with the KS1 compound showed a result that the expression of klotho protein was increased (FIG. 12).

Analysis of MMP-9 Protein Expression Level

Figure 13:
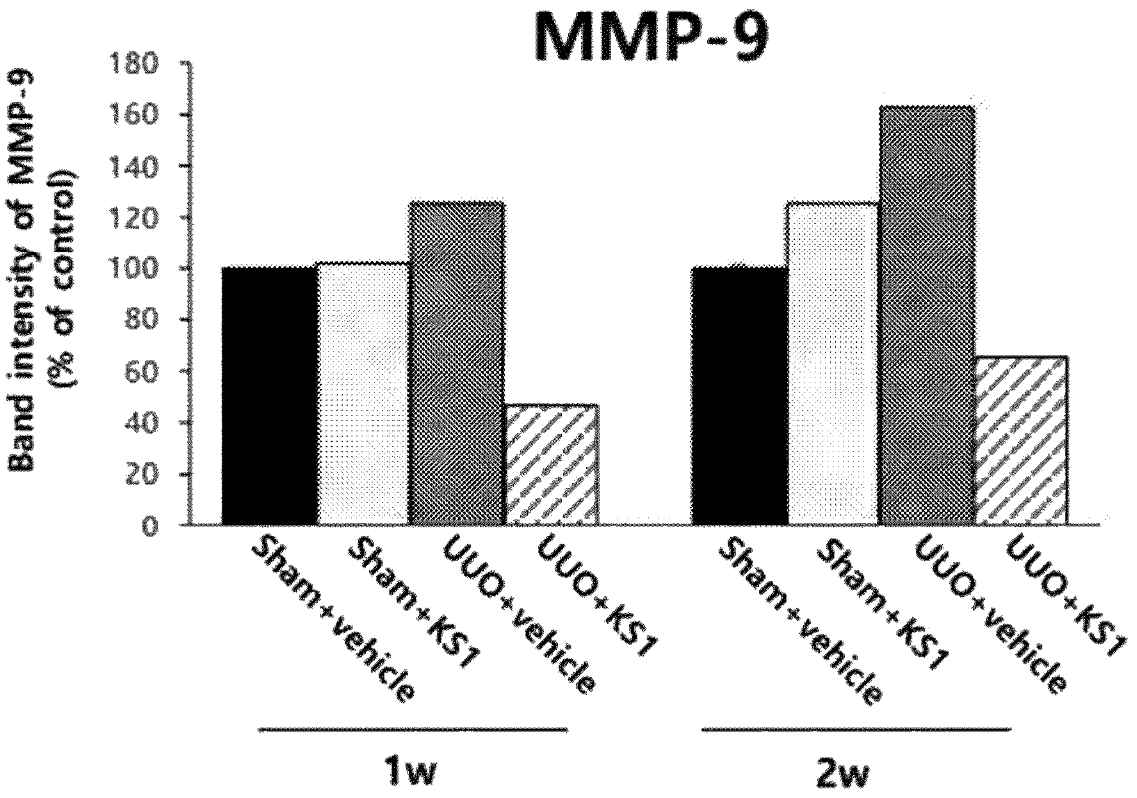
FIG. 13 is a result of analyzing changes in MMP-9 protein expression in a unilateral ureter obstruction model.

As a result of confirming the change in MMP-9 protein, which is an inflammation marker, in the unilateral ureter obstruction model, MMP-9 was increased in the samples of week 1 and week 2 of the unilateral ureter obstruction model which was not treated with KS1, and the case where the sample was treated with KS1 showed a result that the expression level of MMP-9 was remarkably reduced (FIG. 13).

<Experimental Example 7> Analysis of Effect of KS1 Compound (Example 10) in a Chronic Kidney Disease Model For the chronic kidney disease model, 20 db/m mice (10 5-week-old mice, 10 6-week-old mice) and 50 db/db mice (25 5-week-old mice and 25 6-week-old mice) were imported from Jackson Lab, USA, and after the adaptation period, the experiment was started (mouse model number JAX 000642-BKS.Cg-Dock7m+/+Leprdb/j5W/M Wildtype for Dock7m, BKS.Cg-Dock7m+/+Leprdb/j 5W/M Heterozygous for Dock7m). Each group was divided into set1 and set2 due to the large number of mice, with 5-week-old mice as set2, and the experiment was conducted one week later so that all mice were in the experiment from 6 weeks of age. After measuring the body weight, the mice were evenly distributed in each group and fed a normal diet (ND) and a high protein diet (HPD). After 3 weeks on the high protein diet, 2-hour urine samples were collected via a metabolic cage for analysis. Starting at week 5, when urine analysis showed an increase in total protein and microalbumin levels in the high protein diet group, the drug (KS1) was administered orally by gavage daily at different concentrations (2, 10, 50 mg/kg). After 12 weeks of drug administration, mice were sacrificed, and blood and organs were obtained for hematology and tissue analysis. Urine analysis was performed at SCL healthcare center, and blood analysis was performed using I-STAT cartridge (CHEM 8+).

Immunohistochemistry

Figure 14:
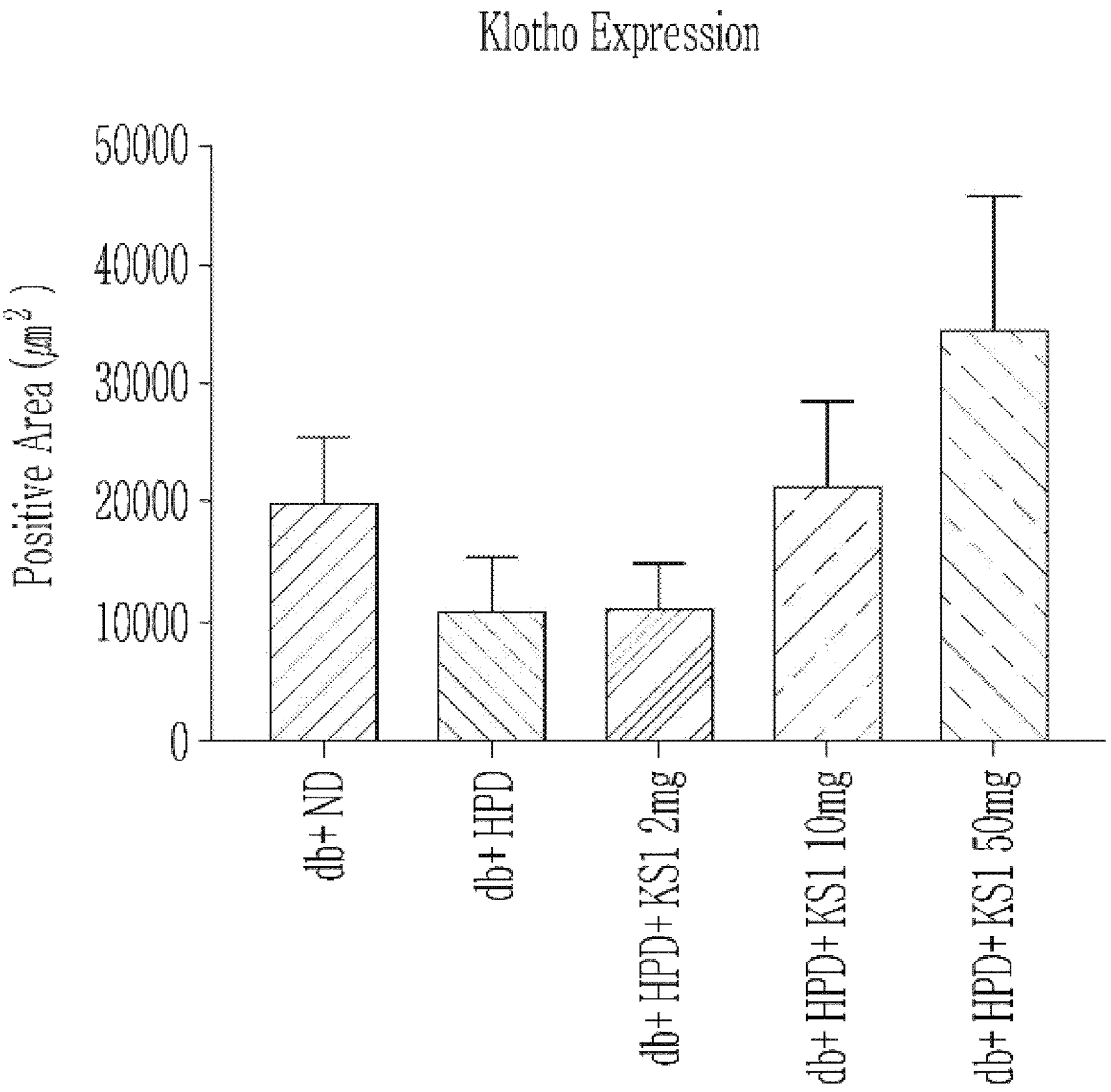
FIGS. 14 and 15 are results of analysis of Klotho protein expression changes in chronic kidney disease models.
Figure 15:
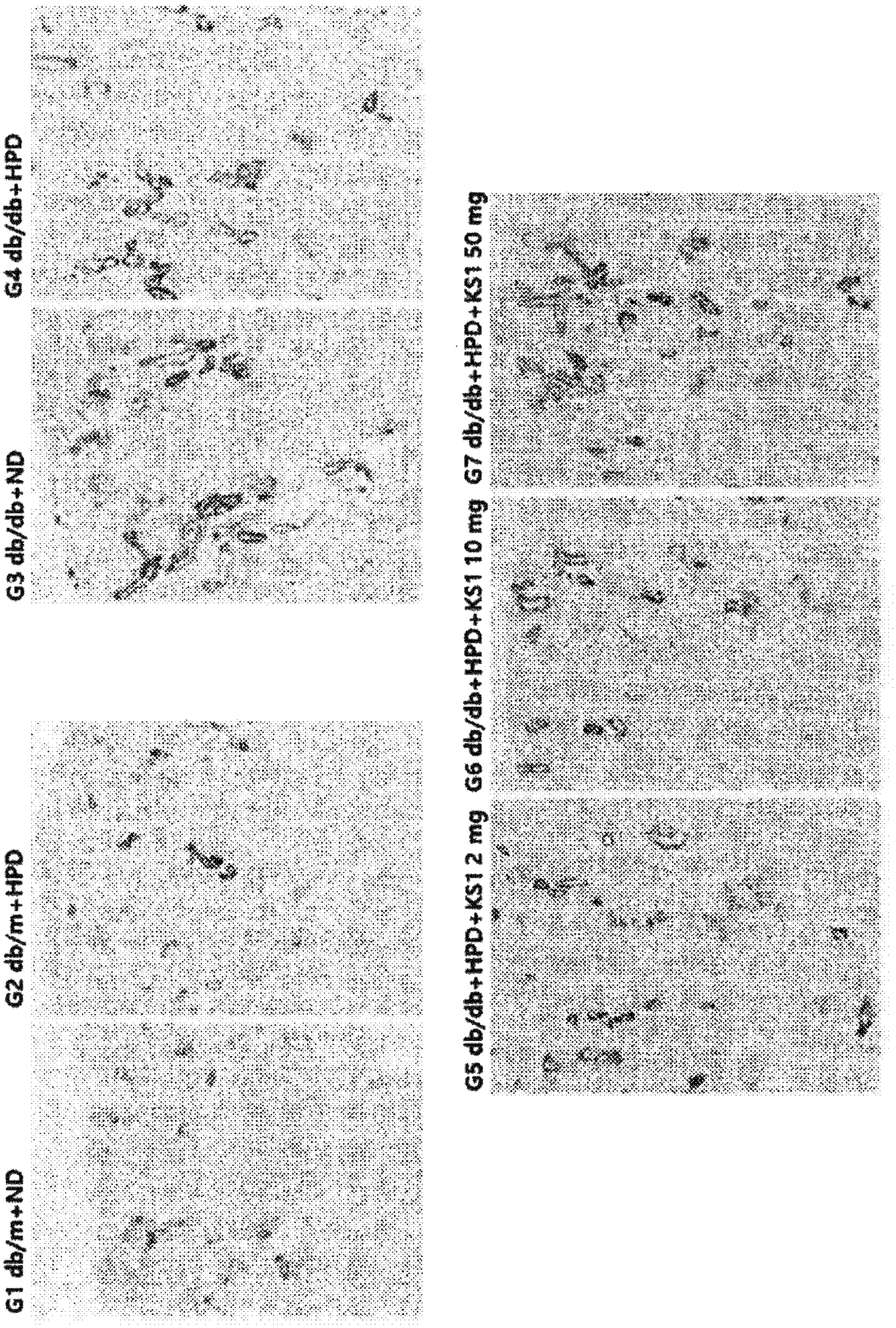

The animals were anesthetized with anesthetic and perfusion-fixed with fixative (Periodate-Lysine-2% paraformaldehyde) through the heart for 8 minutes. Additional fixation was performed at 4° C. for 16 hours or more in the same fixative. After undergoing a dehydration process through an alcohol series, the tissue slides were prepared by embedding in wax and then cutting to 5 μm. After the tissue was hydrated again through the hydration process, it was immersed in a citric acid solution of pH 6 and heated to retrieve the aldehyde-fixed protein. Endogenous peroxidase was then blocked by treatment with 1.7% $H_2O_2$ in methanol for 30 minutes, followed by treatment with 0.5% triton X-100 in PBS for 15 minutes to increase the penetration of the antibody. After blocking with Normal Serum, the primary antibody was treated and incubated overnight. The primary antibody used was Klotho (abcam, ab181373). The next day, the tissue sections were washed with PBS, treated with secondary antibody (vector, immpress kit), and developed with DAB. After development, the sections were counterstained with hematoxylin, dehydrated, mounted, and observed at 100×. Using more than 100 photographs for each group, the expressed areas were quantified using a color image analyzer (TDI Scope Eye version 3.6 for windows; Olympus, Japan) (FIG. 14). Representative photographs of each stained group are shown in FIG. 15. The results confirmed that the expression of klotho protein was statistically significantly ($p<0.05$) increased in mice treated with KS1 compound.

Urine Analysis

Figure 16:
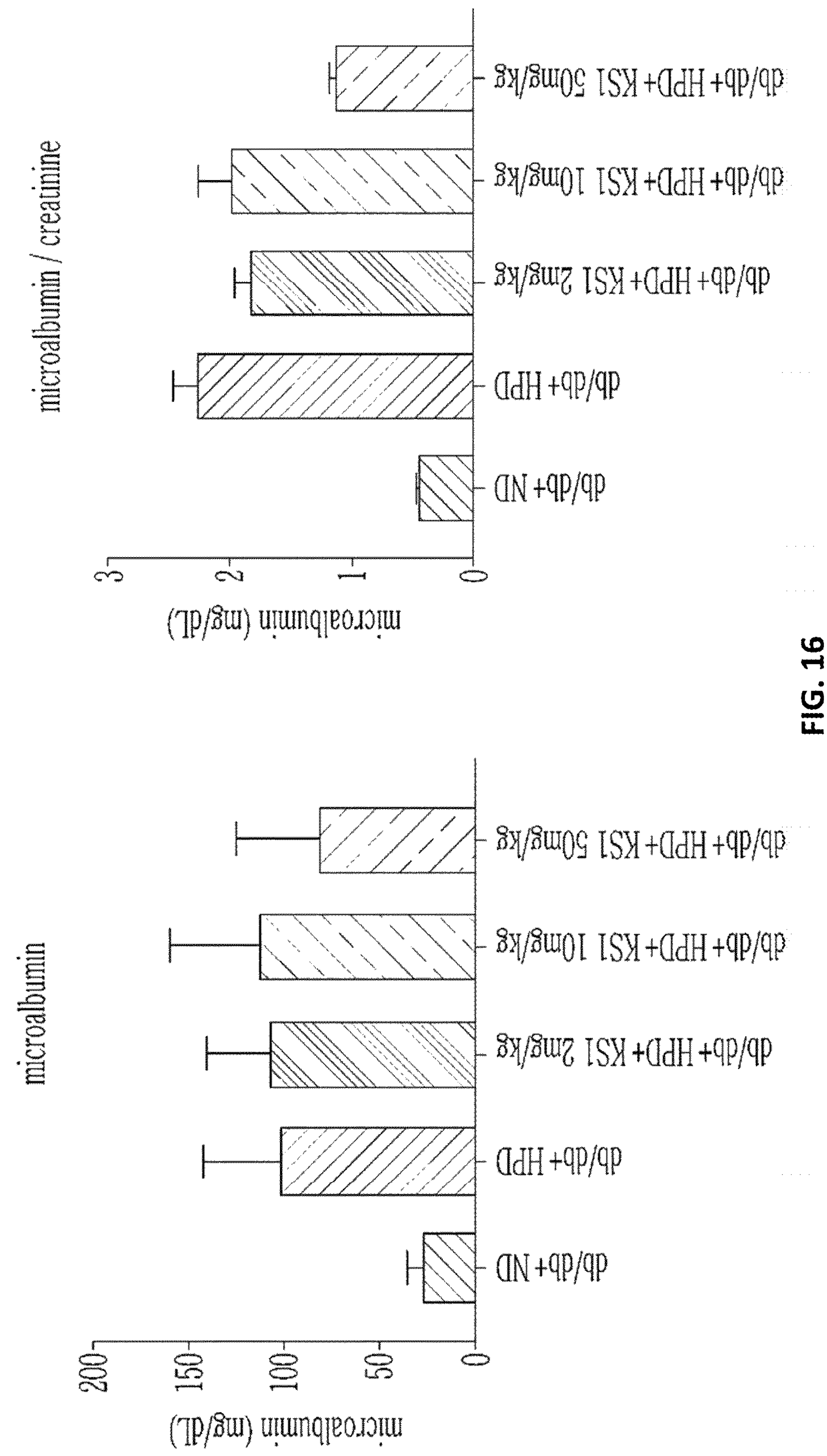
FIG. 16 is a result of analyzing microalbumin level changes in a chronic kidney disease model.

Urine analysis was performed to measure microalbumin levels, and microalbumin levels were expressed in proportion to creatinine values to correct for differences in muscle mass between individual mice. As a result, a statistically significant ($p<0.05$) decrease in microalbumin level was observed in the mice administered with the KS1 compound (FIG. 16).

Blood Analysis

Figure 17:
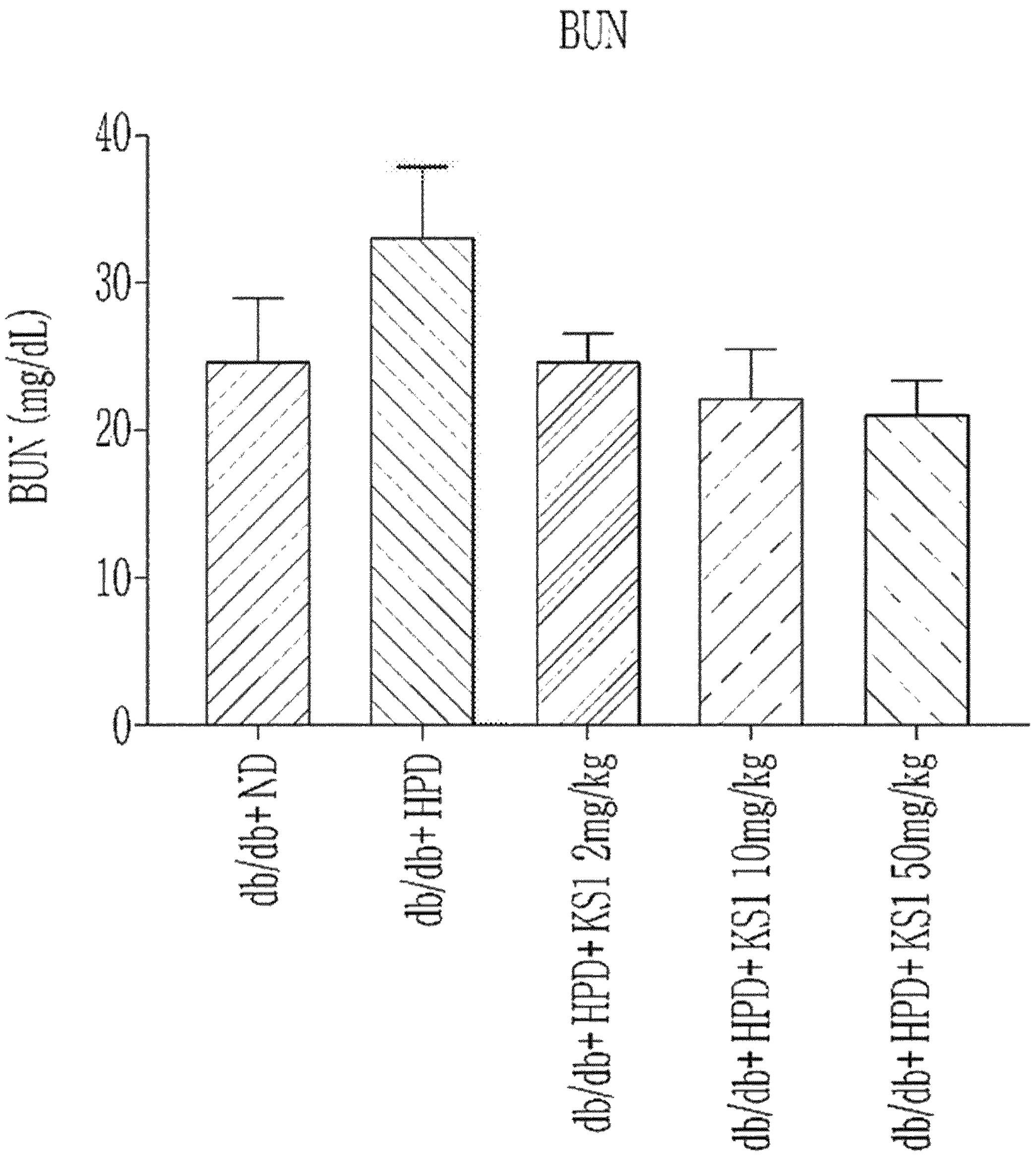
FIG. 17 is a result of analyzing changes in blood urea nitrogen (BUN) levels in a chronic kidney disease model.

As a result of measuring the level of blood urea nitrogen (BUN), a characteristic blood marker of chronic kidney disease, a statistically significant ($p<0.05$) decrease in blood urea nitrogen was confirmed in the mice treated with the KS1 compound. (FIG. 17).

So far, the present invention has been looked at with respect to its preferred embodiments. Those skilled in the art to which the present invention pertains will be able to understand that the present invention can be implemented in a modified form without departing from the essential characteristics of the present invention. Therefore, the disclosed embodiments should be considered from an illustrative rather than a limiting point of view. The scope of the present invention is shown in particular in the claims rather than the foregoing description, and all differences within the equivalent range will be construed as being included in the present invention.

The invention claimed is:

1. A method for preventing or treating chronic kidney disease, the method comprising administering a pharmaceutical composition comprising a compound represented by the following Chemical Formula 1 or a pharmaceutically acceptable salt thereof to a subject in need thereof:

[Chemical Formula 1]

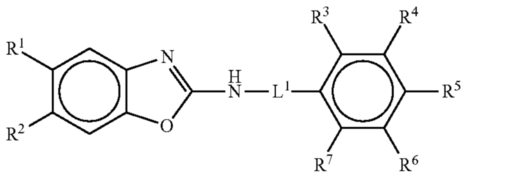

wherein, $L^1$ is a single bond or

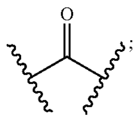 [SMILES: *C(*)=O]

$R^1$ and $R^2$ are each —H, —OH, a $C_{1-10}$ straight or branched alkyl, or a $C_{6-8}$ arylamide, wherein the aryl of the arylamide is optionally substituted with one or more of a halogen, —$NO_2$ and a $C_{1-10}$ straight or branched alkyl halide;

$R^1$ and $R^2$ optionally form a $C_{6-8}$ aryl with a carbon atom to which they are linked; and $R^3$, $R^4$, $R^5$, $R^6$ and $R^7$ are each —H, a halogen, —$NO_2$ or a $C_{1-10}$ straight or branched alkyl.

2. The method of claim 1, wherein $L^1$ is a single bond or

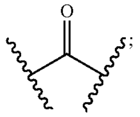

$R^1$ and $R^2$ are each —H, —OH, a $C_{1-5}$ straight or branched alkyl, or a $C_{6-7}$ arylamide, wherein the aryl of the arylamide is optionally substituted with one or more of a halogen, —$NO_2$ and a $C_{1-5}$ straight or branched alkyl halide; $R^1$ and $R^2$ optionally form a $C_{6-7}$ aryl with a carbon atom to which they are linked; and $R^3$, $R^4$, $R^5$, $R^6$ and $R^7$ are each —H, a halogen, —$NO_2$ or a $C_{1-5}$ straight or branched alkyl.

3. The method of claim 1, wherein $L^1$ is a single bond or

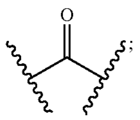 [SMILES: *C(*)=O]

$R^1$ and $R^2$ are each —H, —OH, —$CH_3$, or phenylamide, wherein the phenyl of the phenylamide is optionally substituted with one or more of —Cl, —$NO_2$ and —$CH_2Cl$; $R^1$ and $R^2$ optionally form a phenyl with a carbon atom to which they are linked; and $R^3$, $R^4$, $R^5$, $R^6$ and $R^7$ are each —H, —F, —Cl, —$NO_2$ or —$CH_2CH_3$.

4. The method of claim 1, wherein $L^1$ is a single bond or

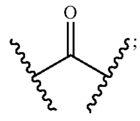 [SMILES: *C(*)=O]

$R^1$ is —H; —OH, —$CH_3$,

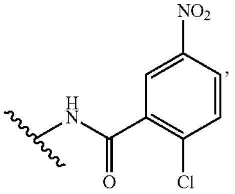

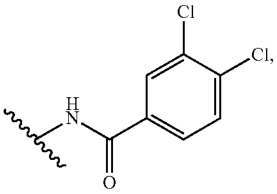

or

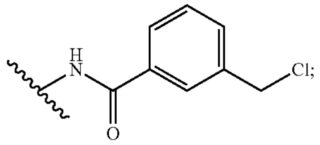

$R^2$ is —H; $R^1$ and $R^2$ optionally form a phenyl with a carbon atom to which they are linked; $R^3$ is —H or —Cl; $R^4$ is —H, —F or —Cl; $R^5$ is —F, —Cl, —$NO_2$, or —$CH_2CH_3$; $R^6$ is —H; and $R^7$ is —H.

5. The method of claim 1, wherein the compound represented by Chemical Formula 1 is any one selected from the following compound group:

1) N-(benzo[d]oxazol-2-yl)-2-chloro-4-nitrobenzamide;
2) 8-methyl-2-[N-(3,4-dichlorophenyl)]aminobenzoxazole;
3) 2-((3,4-dichlorophenyl)amino)benzo[d]oxazol-5-ol;
4) N-(2-(4-ethylphenylamino)benzo[d]oxazol-5-yl)-2-chloro-5-nitrobenzamide;
5) N-(2-(4-ethylphenylamino)benzo[d]oxazol-5-yl)-3,4-dichlorobenzamide;
6) N-(2-(4-ethylphenylamino)benzo[d]oxazol-5-yl)-3-(chloromethyl)benzamide;
7) 2-[N-(3,4-dichlorophenyl)]aminobenzoxazole;
8) N-(3,4-dichlorophenyl)naphtho[2,3-d]oxazol-2-amine;
9) N-(3,4-difluorophenyl)-5-methylbenzo[d]oxazol-2-amine; and
10) N-(3,4-difluorophenyl)benzo[d]oxazol-2-amine.

6. The method of claim 1, wherein the compound represented by the Chemical Formula 1 is a compound represented by the following Chemical Formula 1-1:

[Formula 1-1]

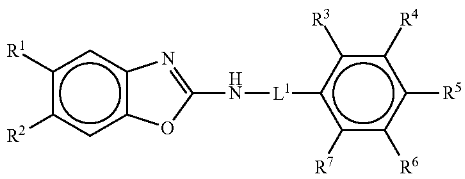

wherein, $L^1$ is a single bond;

$R^1$ and $R^2$ are each —H, or $C_{1-10}$ straight or branched chain alkyl;

$R^3$, $R^4$, $R^5$, $R^6$ and $R^7$ are each —H or halogen.

7. The method of claim 1, wherein the composition increases the expression level of a klotho gene.

8. The method of claim 1, wherein the chronic kidney disease is defined as a disease state in which there is kidney damage or decreased kidney function lasting more than three months.

9. The method of claim 1, wherein the chronic kidney disease comprises one or more conditions selected from the group consisting of chronic nephritis, chronic pyelonephritis, nephrotic syndrome, chronic pyelonephritis, urinary tract infection, diabetic nephropathy, chronic glomerulonephritis, nephroze syndrome, microglomerular sclerosis, membranous nephropathy, and membranoproliferative glomerulonephritis.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: KL-F

<400> SEQUENCE: 1

gatagagaaa aatggcttcc ctcc                                            24


<210> SEQ ID NO 2
<211> LENGTH: 24
<212> TYPE: DNA
<213> ORGANISM: Artificial Sequence
<220> FEATURE:
<223> OTHER INFORMATION: KL-R

<400> SEQUENCE: 2

ggtcggtaaa ctgagacaga gtgg                                            24


<210> SEQ ID NO 3
<211> LENGTH: 24
<212> TYPE: DNA
<213> ORGANISM: Artificial Sequence
<220> FEATURE:
<223> OTHER INFORMATION: GAPDH-F

<400> SEQUENCE: 3

tgacaacttt ggtatcgtgg aagg                                            24


<210> SEQ ID NO 4
<211> LENGTH: 22
<212> TYPE: DNA
<213> ORGANISM: Artificial Sequence
<220> FEATURE:
<223> OTHER INFORMATION: GAPDH-R

<400> SEQUENCE: 4

agggatgatg ttctggagag cc                                              22
```